United States Patent
Oka et al.

(10) Patent No.: US 10,945,678 B2
(45) Date of Patent: Mar. 16, 2021

(54) IMAGE PROCESSING APPARATUS, IMAGE PROCESSING METHOD, AND NON-TRANSITORY STORAGE MEDIUM

(71) Applicant: CANON KABUSHIKI KAISHA, Tokyo (JP)

(72) Inventors: Kazuhito Oka, Tokyo (JP); Kazuhiko Fukutani, Yokohama (JP); Hiroshi Abe, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 20 days.

(21) Appl. No.: 15/990,336

(22) Filed: May 25, 2018

(65) Prior Publication Data
US 2018/0344262 A1 Dec. 6, 2018

(30) Foreign Application Priority Data
Jun. 1, 2017 (JP) .............................. JP2017-109252

(51) Int. Cl.
*A61B 5/00* (2006.01)
*A61B 8/08* (2006.01)
*A61B 5/145* (2006.01)
*A61B 8/00* (2006.01)
*A61B 8/06* (2006.01)
*G16H 50/30* (2018.01)
(Continued)

(52) U.S. Cl.
CPC ............ *A61B 5/742* (2013.01); *A61B 5/0095* (2013.01); *A61B 5/14542* (2013.01); *A61B 5/7275* (2013.01); *A61B 8/0825* (2013.01); *G16H 30/40* (2018.01); *G16H 50/30* (2018.01); *A61B 6/469* (2013.01); *A61B 8/06* (2013.01); *A61B 8/463* (2013.01); *A61B 8/469* (2013.01); *A61B 8/483* (2013.01); *A61B 8/485* (2013.01); *A61B 8/488* (2013.01); *A61B 8/5207* (2013.01)

(58) Field of Classification Search
None
See application file for complete search history.

(56) References Cited

U.S. PATENT DOCUMENTS

| | | | | |
|---|---|---|---|---|
| 2008/0208020 A1* | 8/2008 | Cinbis | ................. | A61B 5/0059 600/323 |
| 2010/0318149 A1* | 12/2010 | Kuhn | ................. | A61B 5/1459 607/18 |

(Continued)

FOREIGN PATENT DOCUMENTS

| | | | |
|---|---|---|---|
| JP | 2013048739 A | * | 3/2013 |
| JP | 2016-147061 A | | 8/2016 |

(Continued)

*Primary Examiner* — Mohammed Rachedine
(74) *Attorney, Agent, or Firm* — Canon U.S.A., Inc., IP Division

(57) ABSTRACT

An image processing apparatus includes an acquisition unit configured to obtain information indicating a discrepancy in the oxygenation index of a blood vessel related to a region of interest based on image data indicating a spatial distribution of an oxygenation index in a subject and information indicating the blood vessel related to the region of interest, and a display control unit configured to display an image on a display unit based on the information indicating the discrepancy in the oxygenation index of the blood vessel related to the region of interest, the image indicating a condition of a tissue included in the region of interest.

17 Claims, 15 Drawing Sheets

(51) Int. Cl.
*G16H 30/40* (2018.01)
*A61B 6/00* (2006.01)

(56) References Cited

U.S. PATENT DOCUMENTS

| | | | | |
|---|---|---|---|---|
| 2013/0245419 A1* | 9/2013 | Oishi | .................. | A61B 5/0095 |
| | | | | 600/407 |
| 2014/0039293 A1* | 2/2014 | Oraevsky | ........... | A61B 5/14552 |
| | | | | 600/407 |
| 2014/0187902 A1* | 7/2014 | Sato | .......................... | G06T 7/12 |
| | | | | 600/407 |
| 2015/0339814 A1* | 11/2015 | Oishi | .................. | G06T 11/008 |
| | | | | 382/131 |

FOREIGN PATENT DOCUMENTS

| | | | | | |
|---|---|---|---|---|---|
| RU | | 2003129845 A | * | 3/2005 | |
| WO | WO-2013084719 A1 | * | 6/2013 | ......... | A61B 5/14551 |

* cited by examiner

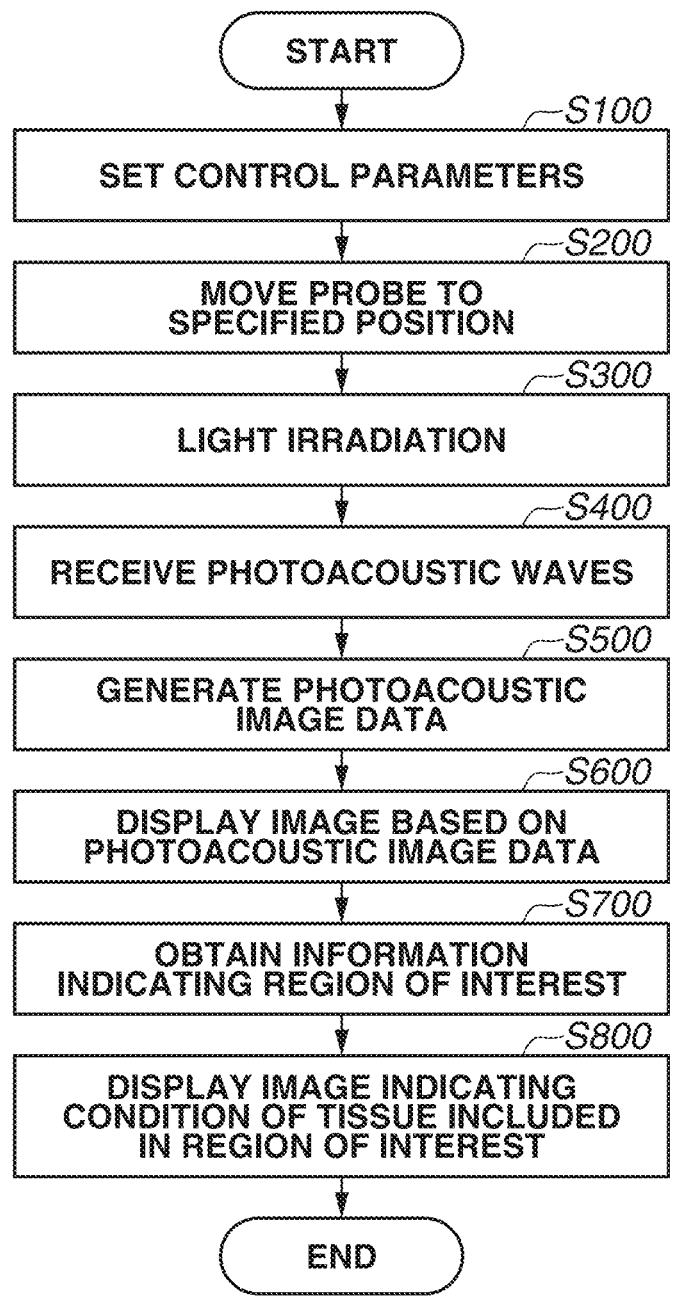

IMAGE PROCESSING APPARATUS, IMAGE PROCESSING METHOD, AND NON-TRANSITORY STORAGE MEDIUM

BACKGROUND OF THE INVENTION

Field of the Invention

The present disclosure relates to an image processing apparatus which uses image data indicating a spatial distribution of an oxygenation index.

Description of the Related Art

There is photoacoustic imaging among imaging techniques for displaying an image based on image data generated by medical diagnostic imaging apparatuses (modalities). The photoacoustic imaging is an imaging technique capable of imaging a spatial distribution of an optical absorber by irradiating the optical absorber with light and receiving acoustic waves occurring from the optical absorber. The application of the photoacoustic imaging to a living body enables imaging of an optical absorber such as a blood vessel containing hemoglobin.

Japanese Patent Application Laid-Open No. 2016-147061 discusses estimating a spatial distribution of oxygen-saturation in the blood inside a living body by photoacoustic imaging. Japanese Patent Application Laid-Open No. 2016-147061 also discusses displaying the estimated spatial distribution of oxygen-saturation.

SUMMARY OF THE INVENTION

With the method for displaying a spatial distribution of an oxygenation index such as oxygen-saturation, a condition of a tissue included in a region of interest may be difficult to be comprehended.

The present disclosure is directed to providing an apparatus that can facilitate the comprehension of the condition of the tissue included in the region of interest.

According to an aspect of the present disclosure, an image processing apparatus includes a first acquisition unit configured to obtain image data indicating a spatial distribution of an oxygenation index in a subject, a second acquisition unit configured to obtain information indicating a region of interest in the subject, a third acquisition unit configured to obtain information indicating a blood vessel related to the region of interest, a fourth acquisition unit configured to obtain information indicating a discrepancy in the oxygenation index of the blood vessel related to the region of interest based on the image data indicating the spatial distribution of the oxygenation index and the information indicating the blood vessel related to the region of interest, and a display control unit configured to display an image on a display unit based on the information indicating the discrepancy in the oxygenation index of the blood vessel related to the region of interest, the image indicating a condition of a tissue included in the region of interest.

Further features of the present disclosure will become apparent from the following description of exemplary embodiments with reference to the attached drawings.

BRIEF DESCRIPTION OF THE DRAWINGS

FIG. 8 is a flowchart of an image display method according to the first exemplary embodiment.

DESCRIPTION OF THE EMBODIMENTS

The present disclosure relates to an image processing method which uses image data indicating a spatial distribution of an oxygenation index. For example, an image processing method according to an exemplary embodiment of the present disclosure can be applied to photoacoustic image data indicating a spatial distribution of an oxygenation index obtained based on photoacoustic waves generated by light irradiation. The oxygenation index is information indicating the degree of oxygenation. Specific examples of the oxygenation index include oxygen-saturation which expresses the proportion of oxygen-bound hemoglobin (oxyhemoglobin) to the hemoglobin in red blood cells. Typically, the oxygen-saturation of blood is information having a value of 0% to 100%. Other examples of the oxygenation index will be described below.

An exemplary embodiment of the present disclosure will be described below by taking an example of photoacoustic image data indicating a spatial distribution of oxygen-saturation obtained based on photoacoustic waves as an oxygenation index.

Figure 1A:
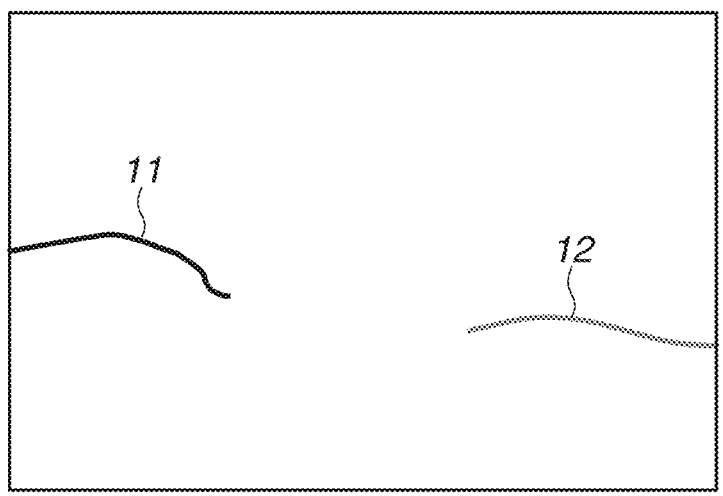
FIGS. 1A and 1B are schematic diagrams illustrating an image display method according to a comparative example.

FIG. 1A illustrates a photoacoustic image indicating a spatial distribution of oxygen-saturation obtained based on photoacoustic waves generated by light irradiation of a subject. The photoacoustic image in FIG. 1A includes images of blood vessels 11 and 12. In FIG. 1A, different tone levels of the images represent different levels of oxygen-saturation. More specifically, in FIGS. 1A and 1B, blackish blood vessels have higher levels of oxygen-saturation. Whitish blood vessels have lower level of oxygen-saturation. In FIG. 1A, the blood vessel 11 has an oxygen-saturation of 99%, and the blood vessel 12 an oxygen-saturation of 85%.

Figure 1B:
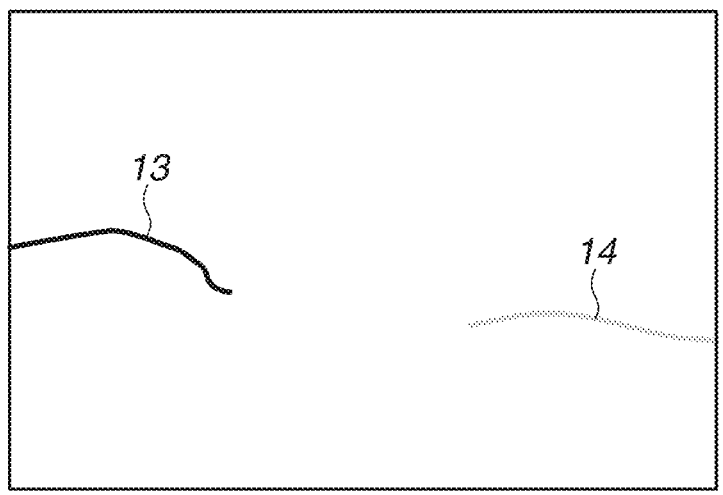

FIG. 1B illustrates a photoacoustic image indicating a spatial distribution of oxygen-saturation obtained based on photoacoustic waves. The photoacoustic image in FIG. 1B is based on photoacoustic waves generated by light irradiation of a subject different from that in FIG. 1A. The photoacoustic image in FIG. 1B includes image data of blood vessels 13 and 14. In FIG. 1B, the blood vessel 13 has an oxygen-saturation of 99%, and the blood vessel 14 an oxygen-saturation of 65%.

Suppose that the user observes the photoacoustic images in FIGS. 1A and 1B for diagnosis, based on an assumption that the oxygen consumption of a tissue changes with the degree of malignancy of the tumor. In such a case, it is conceivable that it is difficult to find out the condition of the tissue because just displaying images indicating a spatial distribution of oxygen-saturation as illustrated in FIGS. 1A and 1B cannot facilitate the comprehension of the oxygen consumption in the tissue.

The inventor has conceived an idea of estimating the condition of a tissue included in a region of interest and displaying an image indicating the condition of the tissue based on an oxygenation index such as oxygen-saturation of blood vessels related to the region of interest. An example of an image processing method to be performed by a computer serving as an image processing apparatus will be described below.

Figure 2A:
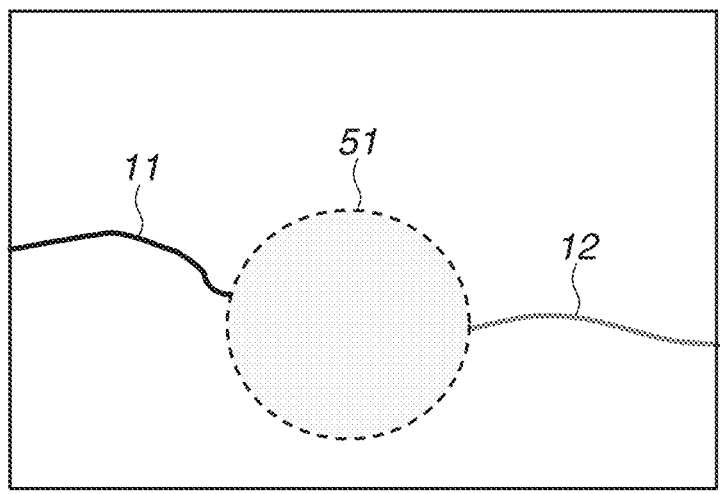
FIGS. 2A and 2B are schematic diagrams illustrating a mode of an image display method according to the present disclosure.

For example, suppose that the user designates a region including a tissue 51 to be a region of interest as illustrated in FIG. 2A. In such a case, a blood vessel 11 (artery) for supplying blood to the tissue 51 and a blood vessel 12 (vein) for draining the blood in which oxygen is consumed by the tissue 51 are calculated. The amount of change between the oxygen-saturation of the blood vessel 11 (artery) and the oxygen-saturation of the blood vessel 12 (vein) is then calculated. A difference between the oxygen-saturation (99%) of the blood vessel 11 and the oxygen-saturation (85%) of the blood vessel 12 here is 14%.

Figure 2B:
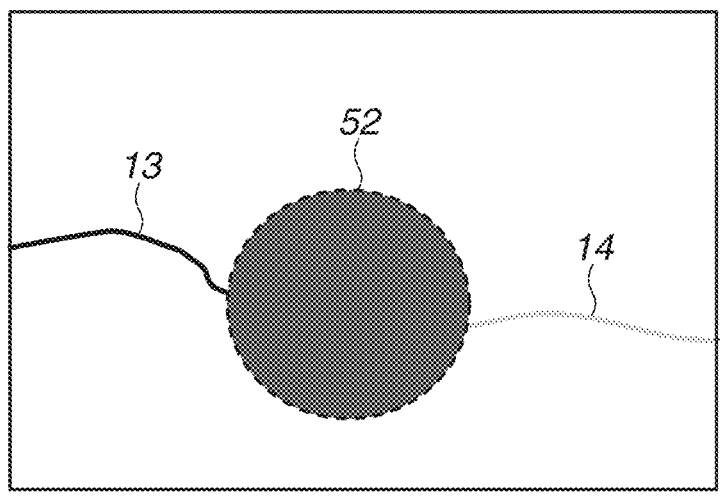

Now, suppose that a region including a tissue 52 is similarly designated as a region of interest in the image in FIG. 2B. In such a case, a difference between the oxygen-saturation (99%) of the blood vessel 13 and the oxygen-saturation (65%) of the blood vessel 14 is 34%.

A display mode of the image of the region of interest is changed according to the amount of change in the oxygen-saturation of the blood vessels related to the region of interest. For example, in FIGS. 2A and 2B, the display color of the region of interest is changed according to the amount of change in the oxygen-saturation of the blood vessels related to the region of interest. In FIGS. 2A and 2B, the display color of the image of the region of interest changes from white to black as the difference in the oxygen-saturation of the blood vessels related to the region of interest increases. As a result, the display color in FIG. 2B in which the blood vessels related to the region of interest have a relatively large difference in the oxygen-saturation is darker than in FIG. 2A. The user can thus easily find out that the tissue 52 is likely to have a high degree of malignancy. That is, in the display in FIGS. 2A and 2B, the display mode is changed based on the condition of the tissue included in the region of interest.

While an example of calculating a difference is described here as the amount of change in the oxygenation index of the blood vessels related to the region of interest, the amount of change is not limited to the difference. The amount of change may be expressed by using any index as long as the index includes information indicating a discrepancy in the oxygenation index of the blood vessels related to the region of interest. For example, a ratio may be used as the information indicating the discrepancy in the oxygenation index of the blood vessels related to the region of interest. Information indicating variations in the oxygenation index of the blood vessels related to the region of interest may be used as the information indicating the discrepancy in the oxygenation index of the blood vessels related to the region of interest. Conventional indexes indicating variations, such as a variance and a standard deviation, may be used for the variations. In summary, information indicating at least one of a difference, a ratio, and variations in the oxygenation index of the blood vessels related to the region of interest may be used as the information indicating the discrepancy in the oxygenation index of the blood vessels related to the region of interest.

The condition of a tissue may be the degree of malignancy of the tissue, or the possibility for the tissue to be malignant.

By such an image display method, the condition of the tissue which is difficult to be comprehended from only the display of the spatial distribution of the oxygenation index can be easily found out.

Figure 3A:
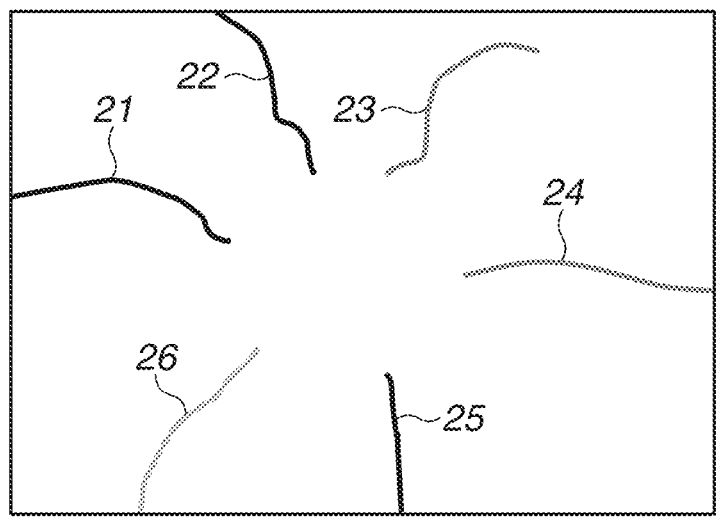
FIGS. 3A and 3B are schematic diagrams illustrating the image display method according to the comparative example.

The present exemplary embodiment is also applicable to an image including three or more blood vessels. FIG. 3A illustrates image data which includes six blood vessels 21 to 26. In FIG. 3A, the blood vessel 21 has an oxygen-saturation of 99%, the blood vessel 22 has an oxygen-saturation of 97%, the blood vessel 23 has an oxygen-saturation of 88%, the blood vessel 24 has an oxygen-saturation of 84%, the blood vessel 25 has an oxygen-saturation of 98%, and the blood vessel 26 has an oxygen-saturation of 80%.

Figure 3B:
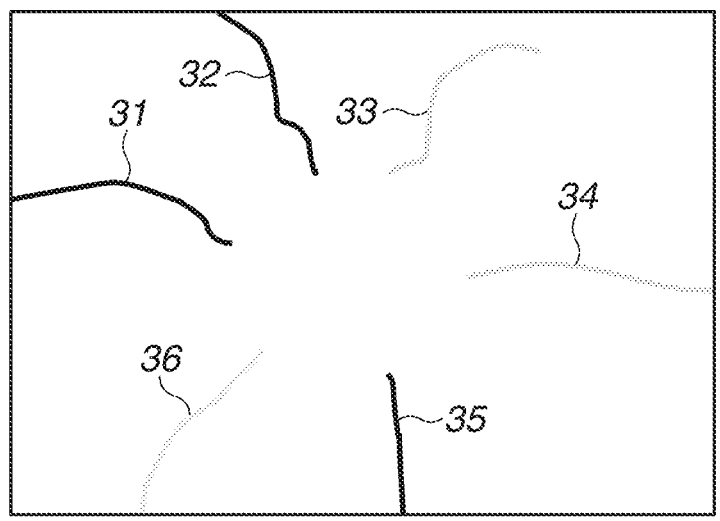

FIG. 3B illustrates image data which includes six blood vessels 31 to 36. In FIG. 3B, the blood vessel 31 has an oxygen-saturation of 99%, the blood vessel 32 has an oxygen-saturation of 97%, the blood vessel 33 has an oxygen-saturation of 70%, the blood vessel 34 has an oxygen-saturation of 64%, the blood vessel 35 has an oxygen-saturation of 98%, and the blood vessel 36 has an oxygen-saturation of 61%.

In the case of making a diagnosis by observing the images in FIGS. 3A and 3B, as with FIGS. 1A and 1B, it is conceivable that it is difficult to comprehend the conditions of the tissues included in the images from only the display of the spatial distributions of oxygen-saturation. Then, the inventor has conceived an idea of segmenting blood vessels related to the region of interest into blood vessels for supplying blood to the tissue included in the region of interest and blood vessels for carrying blood flowing away from the tissue included in the region of interest. The inventor has further conceived an idea of estimating and displaying the condition of the tissue included in the region of interest based on the oxygenation index such as oxygen-saturation of the segmented blood vessels.

Figure 4A:
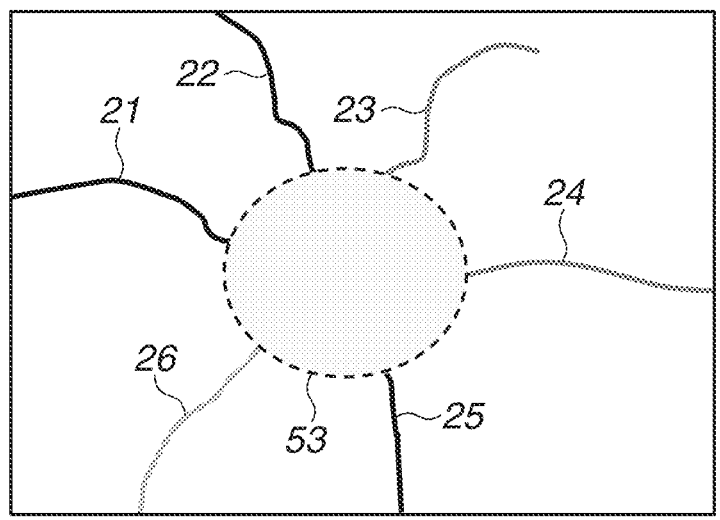
FIGS. 4A and 4B are schematic diagrams illustrating a mode of the image display method according to the present disclosure.

For example, as illustrated in FIG. 4A, if the user designates a region including a tissue 53 as the region of interest, the blood vessels 21, 22, and 25 (blood vessels corresponding to arteries) for supplying blood to the tissue 53 are identified. The blood vessels 23, 24, and 26 (blood vessels corresponding to veins) for carrying blood flowing away from the tissue 53 are also identified.

A representative value of the oxygen-saturation of the blood vessels 21, 22, and 25 corresponding to arteries is further calculated. A representative value of the oxygen-saturation of the blood vessels 23, 24, and 26 corresponding to veins is also calculated. The amount of change between the representative value of the oxygen-saturation of the blood vessels 21, 22, and 25 corresponding to arteries and the representative value of the oxygen-saturation of the blood vessels 23, 24, and 26 corresponding to veins is then calculated.

For example, in the case of determining an average as a representative value, the representative value of the oxygen-saturation of the blood vessels 21, 22, and corresponding to arteries is 98%. In the case of determining an average as a representative value, the representative value of the oxygen-saturation of the blood vessels 23, 24, and 26 corresponding to veins is 84%. In such a case, a difference between the representative value (98%) of the oxygen-saturation of the blood vessels 21, 22, and 25 corresponding to arteries and the representative value (84%) of the oxygen-saturation of the blood vessels 23, 24, and 26 corresponding to veins is 14%.

Similarly, suppose that in the image illustrated FIG. 3B, a region including a tissue 54 is designated as the region of interest. In such a case, the representative value of the oxygen-saturation of the blood vessels 31, 32, and 35 corresponding to arteries is 99%. The representative value of the oxygen-saturation of the blood vessels 33, 34, and 36 corresponding to veins is 65%. In the image in FIG. 3B, a difference between the representative value (98%) of the oxygen-saturation of the blood vessels 31, 32, and 35 corresponding to arteries and the representative value (65%) of the oxygen-saturation of the blood vessels 33, 34, and 36 corresponding to veins is 33%.

Figure 4B:
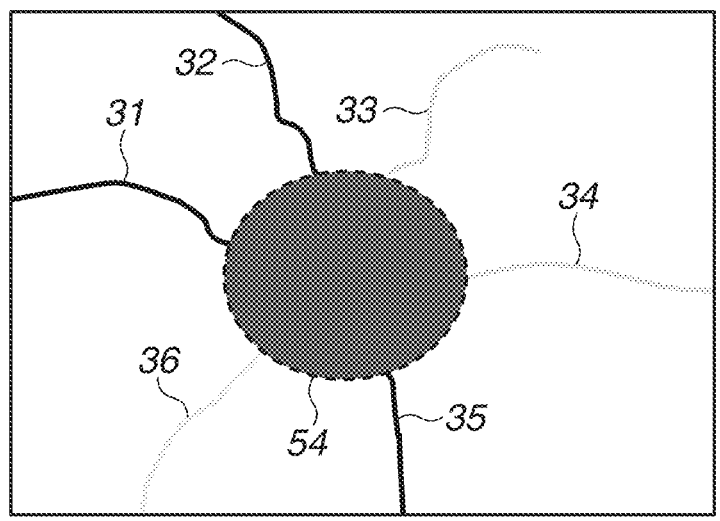

In FIGS. 4A and 4B, like FIGS. 2A and 2B, the display mode of the image of the region of interest is changed according to the amount of change in the representative value of oxygen-saturation. The difference in the representative value of the oxygen-saturation in the image in FIG. 4B is greater than that in the representative value of the oxygen-saturation in the image in FIG. 4A. The display color of the image of the tissue 54 in FIG. 4B is therefore darker than that of the image of the tissue 53 in FIG. 4A. The user can easily find out, by observing the images, that the degree of malignancy of the tissue 53 can be low and that of the tissue 54 can be high.

While a tissue can include blood vessels, such blood vessels are not visualized in the foregoing examples.

A suitable exemplary embodiment of the present disclosure will be described below with reference to the drawings. Dimensions, materials, shapes, and a relative arrangement of the components described below shall be changed as appropriate depending on a configuration and various conditions of the apparatus to which the exemplary embodiment is applied. The following description is not intended to limit the scope of the present invention.

A first exemplary embodiment describes an example where a photoacoustic apparatus obtains a spatial distribution of oxygen-saturation as an oxygenation index. The first exemplary embodiment deals with a case where the user designates a region of interest on photoacoustic image data obtained by the photoacoustic apparatus. A configuration and an information processing method of the photoacoustic apparatus according to the present exemplary embodiment will be described below.

Figure 5:
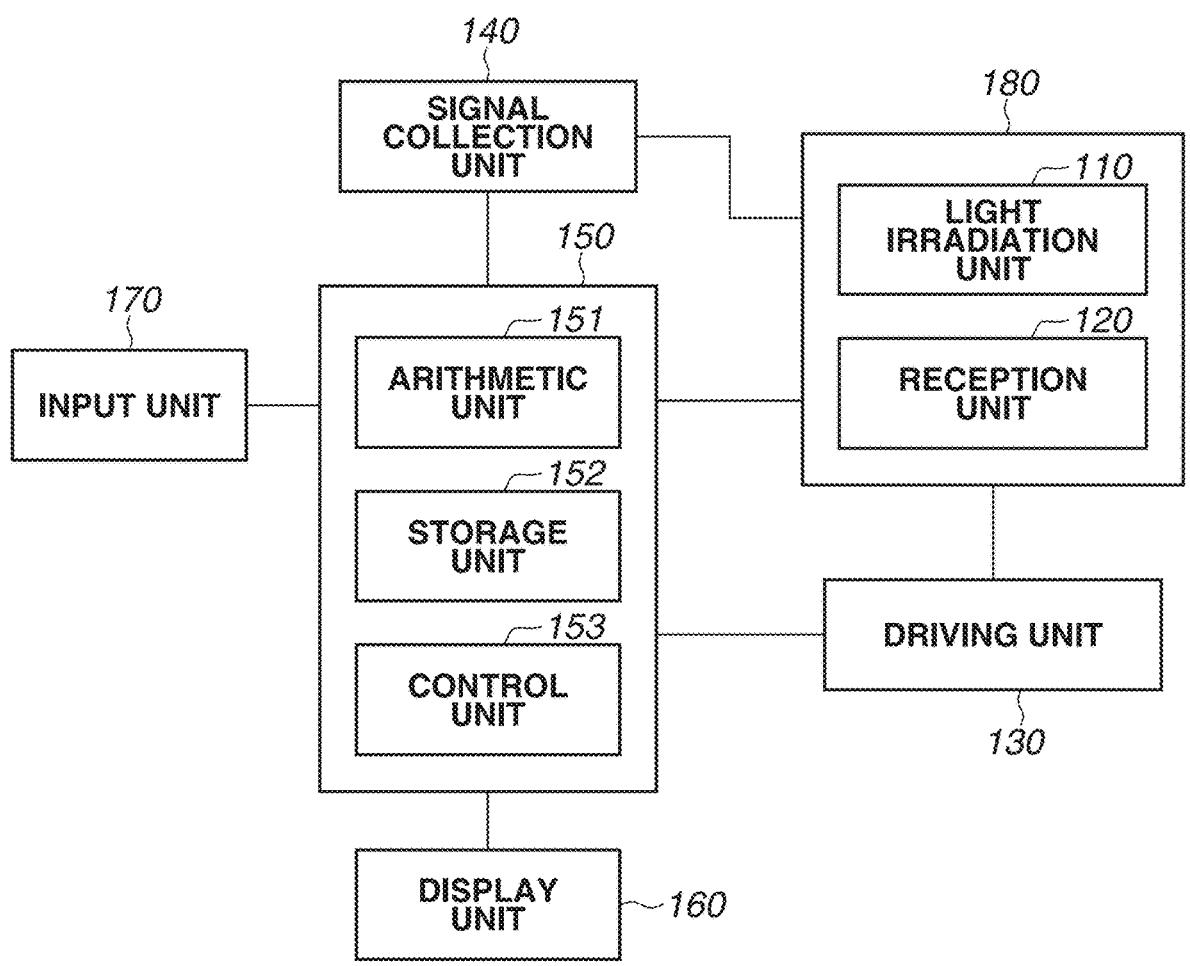
FIG. 5 is a block diagram illustrating a photoacoustic apparatus according to a first exemplary embodiment.

The configuration of the photoacoustic apparatus according to the present exemplary embodiment will be described with reference to FIG. 5. FIG. 5 is a schematic block diagram of the entire photoacoustic apparatus. The photoacoustic apparatus according to the present exemplary embodiment includes a probe 180, a driving unit 130, a signal collection unit 140, a computer 150, a display unit 160, and an input unit 170. The probe 180 includes a light irradiation unit 110 and a reception unit 120.

Figure 6A:
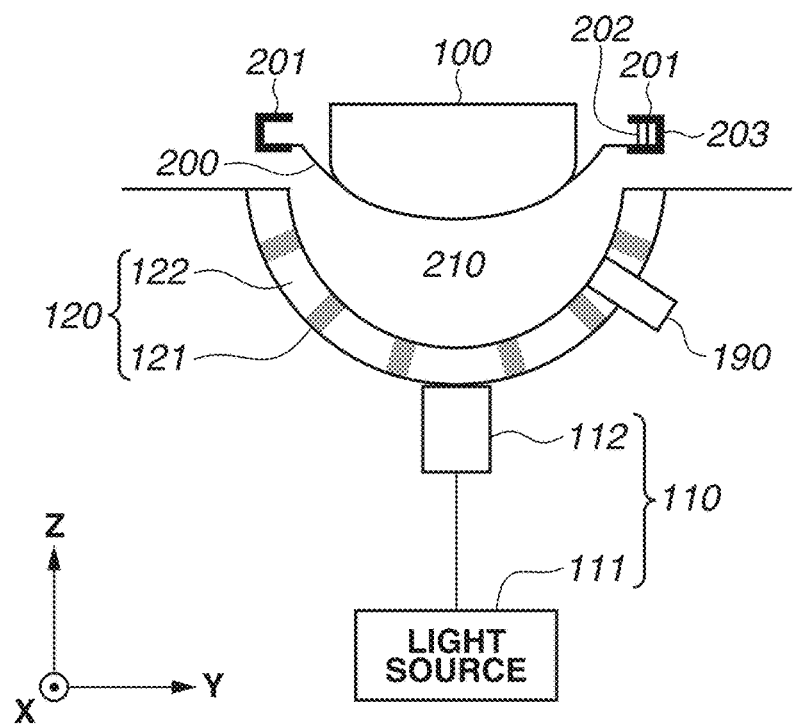
FIGS. 6A and 6B are schematic diagrams illustrating a probe according to the first exemplary embodiment.
Figure 6B:
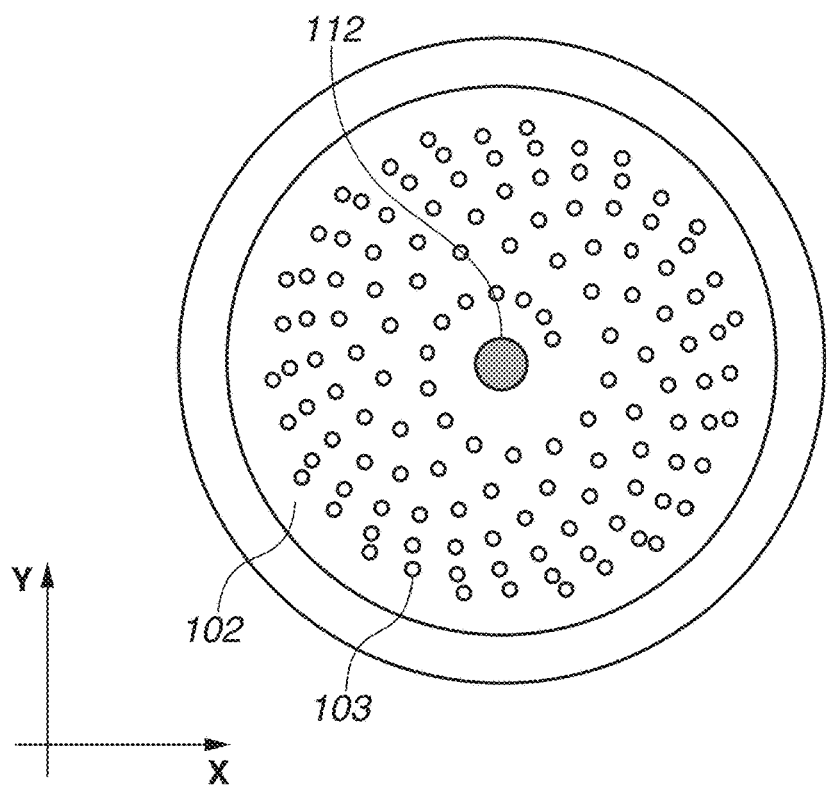

FIGS. 6A and 6B illustrate schematic diagrams of the probe 180 according to the present exemplary embodiment. A subject 100 is the object to be measured. The driving unit 130 drives the light irradiation unit 110 and the reception unit 120 to perform mechanical scanning. The light irradiation unit 110 irradiates the subject 100 with light, and acoustic waves occur in the subject 100. Acoustic waves occurring from light by a photoacoustic effect will also be referred to as photoacoustic waves. The reception unit 120 receives the photoacoustic waves and outputs an electrical signal (photoacoustic signal) which is an analog signal.

The signal collection unit 140 converts the analog signal output from the reception unit 120 into a digital signal, and outputs the digital signal to the computer 150. The computer 150 stores the digital signal output from the signal collection unit 140 as signal data derived from ultrasonic waves or photoacoustic waves.

The computer 150 generates photoacoustic image data expressing a two- or three-dimensional spatial distribution of information (subject information) about the object 100 by performing signal processing on the stored digital signal. The computer 150 displays an image based on the obtained photoacoustic image data on the display unit 160. A doctor who is the user can make a diagnosis by observing the image displayed on the display unit 160. The displayed image is stored into a memory in the computer 150 or a data management system connected to the modality via a network, based on a storage instruction from the user or the computer 150.

The computer 150 also performs drive control on the components included in the photoacoustic apparatus. The display unit 160 may display a graphical user interface (GUI) aside from the image generated by the computer 150. The input unit 170 is configured such that the user can input information. By using the input unit 170, the user can make operations to start and end measurement and give a storage instruction for a generated image.

Details of the components of the photoacoustic apparatus according to the present exemplary embodiment will be described below.

(Light Irradiation Unit 110)

The light irradiation unit 110 includes a light source 111 which emits light, and an optical system 112 which guides the light emitted from the light source 111 to the subject 100. The light may include pulsed light of rectangular waves or triangular waves.

The light emitted from the light source 111 may have a pulse width of 1 ns or more and not more than 100 ns. The light wavelength may be in the range of approximately 400 nm to 1600 nm. For high resolution imaging of blood vessels, light of wavelengths at which the absorption by blood vessels is high (400 nm or more and not more than 700 nm) may be used. For imaging of deep parts of a living body, light of wavelengths at which the absorption by background tissues (water and fat) of the living body is typically low (700 nm or more and not more than 1100 nm) may be used.

A laser or a light-emitting diode may be used as the light source 111. To use a plurality of wavelengths of light for measurement, the light source 111 may be a wavelength-changeable one. To irradiate the subject 100 with a plurality of wavelengths of light, a plurality of light sources for generating light of respective different wavelengths may be provided, and the light sources may alternately irradiate the subject 100. If a plurality of light sources is used, the light sources will be referred to collectively as a light source. Various lasers, including a solid laser, gas laser, dye laser, and semiconductor laser, may be used. For example, a pulse laser such as a Nd:YAG laser or an alexandrite laser may be used as the light source. A Ti:Sa laser or an optical parametric oscillator (OPO) laser that uses Nd:YAG laser light as excitation light may be used as the light source. A flash lamp or a light-emitting diode may be used as the light source 111. A microwave source may be used as the light source 111.

The optical system 112 may use optical elements such as a lens, a mirror, and an optical fiber. If the subject 100 is a breast, a light emission part of the optical system 112 may include a diffusion plate for diffusing light so that the beam diameter of the pulsed light is expanded for irradiation. In the case of a photoacoustic microscope, the light emission part of the optical system 112 may include a lens so that the subject 100 is irradiated with a focused beam for enhanced resolution.

The subject 100 may be directly irradiated with light from the light source 111, without the optical system 112 included in the light irradiation unit 110.

(Reception Unit 120)

The reception unit 120 includes transducers 121 which output electrical signals by receiving acoustic waves, and a support 122 which supports the transducers 121. The transducers 121 may be transmission units for transmitting acoustic waves. Transducers serving as reception units and transducers serving as transmission units may be either identical (common) transducers or different ones.

The transducers 121 may include members made of piezoelectric ceramic materials typified by PZT (lead zirconate titanate), or polymeric piezoelectric film materials typified by polyvinylidene difluoride (PVDF). Elements other than piezoelectric elements may be used. For example, capacitive micro-machined ultrasound transducers (CMUTs) and transducers using a Fabry-Perot interferometer may be used. Any transducers may be used as long as electrical signals can be output by receiving acoustic waves. The signals to be obtained by the transducers are time-resolved signals. In other words, the amplitudes of the signals to be obtained by the transducers express values based on the sound pressures to be received by the transducers (for example, values in proportion to the sound pressures) at each time.

Photoacoustic waves typically include frequency components of 100 kHz to 100 MHz. Transducers capable of detecting such frequencies can be used as the transducers 121.

The support 122 may be made of a metal material having high mechanical strength. To increase irradiation light incident on the subject 100, the surface of the support 122 on the subject 100 side may be mirror-finished or processed to scatter light. In the present exemplary embodiment, the support 122 has a hemispherical enclosure shape, and is configured such that a plurality of transducers 121 can be supported on the hemispherical enclosure. In such a case, the directional axes of the transducers 121 arranged on the support 122 concentrate near the center of curvature of the hemisphere. This enhances image quality near the center of curvature if an image is formed by using the signals output from the plurality of transducers 121. The support 122 may have any configuration as long as the transducers 121 can be supported. The support 122 may be configured such that the plurality of transducers 121 is arranged on a flat or curved surface called a one-dimensional (1D) array, 1.5D array, 1.75D array, or 2D array. The plurality of transducers 121 corresponds to a plurality of reception units.

The support 122 may also function as a container for storing an acoustic matching material 210. In other words, the support 122 may serve as a container for providing the acoustic matching material 210 between the transducers 121 and the subject 100.

The reception unit 120 may include an amplifier for amplifying time series of analog signals output from the transducers 121. The reception unit 120 may include an analog-to-digital (A/D) converter for converting the time series of analog signals output from the transducers 121 into time series of digital signals. In other words, the reception unit 120 may include the signal collection unit 140 to be described below.

To enable detection of acoustic waves at various angles, the transducers 121 may ideally be arranged to surround the subject 100 in all directions. If the subject 100 is too large to arrange the transducers 121 to surround in all directions, the transducers 121 may be arranged on the hemispherical support 122 to approximate the state of surrounding the subject 100 in all directions.

The arrangement and the number of transducers 121 and the shape of the support 122 may be optimized according to the subject 100. Any reception unit 120 may be used in the present exemplary embodiment.

The space between the reception unit 120 and the subject 100 is filled with a medium through which photoacoustic waves can propagate. A material that can propagate acoustic waves, provides matching in acoustic characteristic at the interfaces with the subject 100 and the transducers 121, and has as high photoacoustic wave transmittance as possible is used as the medium. Examples of such a medium may include water and an ultrasound gel.

FIG. 6A illustrates a side view of the probe 180. FIG. 6B illustrates a top view of the probe 180 (a view as seen from above on the plane of FIG. 6A). The probe 180 according to the present exemplary embodiment in FIGS. 6A and 6B includes the reception unit 120 which includes the plurality of transducers 121 three-dimensionally arranged on the hemispherical support 122 having an opening. In the probe 180 in FIGS. 6A and 6B, the light emission part of the optical system 112 is arranged at the bottom of the support 122.

In the present exemplary embodiment, as illustrated in FIGS. 6A and 6B, the subject 100 makes contact with a holding unit 200 and is thereby held in shape. In the present exemplary embodiment, if the subject 100 is a breast, an opening for inserting a breast is formed in a bed which supports the examinee in a prone position. The breast to be measured is expected to be vertically hung from the opening.

The space between the reception unit 120 and the holding unit 200 is filled with a medium (acoustic matching member 210) through which photoacoustic waves can propagate. A material that can propagate photoacoustic waves, provides matching in acoustic characteristic at the interfaces with the subject 100 and the transducers 121, and has as high photoacoustic wave transmittance as possible is used as the medium. Examples of such a medium may include water and an ultrasound gel.

The holding unit 200 is used to hold the shape of the subject 100 during measurement. If the subject 100 is held by the holding unit 200, the movement of the subject 100 can be suppressed and the position of the subject 100 can be kept inside the holding unit 200. The holding unit 200 may be made of a resin material such as polycarbonate, polyethylene, or polyethylene terephthalate.

It is desirable that the holding unit 200 is made of a material having a hardness capable of holding the subject 100. The holding unit 200 may be made of a material that transmits the light used for measurement. The holding unit 200 may be made of a material having impedance similar to that of the subject 100. If the subject 100 has a curved surface like a breast, the holding unit 200 may be molded in a recessed shape. In such a case, the subject 100 can be inserted into the recessed portion of the holding unit 200.

The holding unit 200 is attached to a mount unit 201. The mount unit 201 may be configured such that a plurality of types of holding units 200 can be interchanged according to the size of the subject 100. For example, the mount unit 201 may be configured such that holding units 200 having different radii of curvature or different centers of curvature can be interchanged.

The holding unit 200 may be provided with a tag 202 in which information about the holding unit 200 is registered. For example, information such as the radius of curvature, the center of curvature, sound speed, and an identifier (ID) of the holding unit 200 can be registered in the tag 202. The information registered in the tag 202 is read by a reading unit 203 and transferred to the computer 150. To easily read the tag 202 when the holding unit 200 is attached to the mount unit 201, the reading unit 203 may be provided on the mount unit 201. For example, the tag 202 is a barcode, and the reading unit 203 is a barcode reader.

(Driving Unit 130)

The driving unit 130 is a component for changing a relative position between the subject 100 and the reception unit 120. In the present exemplary embodiment, the driving unit 130 is a device for moving the support 122 in X and Y directions. More specifically, the driving unit 130 is a motor-driven XY stage including a stepping motor. The driving unit 130 includes a motor such as a stepping motor for generating driving force, a drive mechanism for transmitting the driving force, and a position sensor for detecting position information about the reception unit 120. Examples of the driving mechanism may include a lead screw mechanism, a link mechanism, a gear mechanism, and a hydraulic mechanism. Examples of the position sensor may include potentiometers using an encoder or a variable resistor.

The driving unit 130 is not limited to one that changes the relative position between the subject 100 and the reception unit 120 in the X and Y directions (two-dimensionally), and may change the relative position one- or three-dimensionally. The moving path may be flatly scanned in a spiral shape or in a line-and-space pattern. The moving path may be three-dimensionally tilted along the body surface. The probe 180 may be moved to keep a certain distance from the surface of the subject 100. Here, the driving unit 130 may measure the amount of movement of the probe 180 by monitoring the number of rotations of the motor.

The driving unit 130 may move the subject 100 with the reception unit 120 fixed, as long as the relative position between the subject 100 and the reception unit 120 can be changed. In the case of moving the subject 100, the driving unit 130 may be configured to move the subject 100 by moving the holding unit 200 holding the subject 100. Both the subject 100 and the reception unit 120 may be moved.

The driving unit 130 may move the relative position continuously or in a step-and-repeat manner. The driving unit 130 may be a motor-driven stage for moving the relative position along a programmed track. The driving unit 130 may be a manual stage. In other words, the photoacoustic apparatus may be of handheld type without the driving unit 130, in which the user can grip and operate the probe 180.

In the photoacoustic apparatus of handheld type, the probe 180 includes a grip portion such that the user can grip the probe 180.

In the present exemplary embodiment, the driving unit 130 simultaneously drives and scans the light irradiation unit 110 and the reception unit 120. However, the driving unit 130 may drive only the light irradiation unit 110 or only the reception unit 120.

(Signal Collection Unit 140)

The signal collection unit 140 includes an amplifier which amplifies the analog electrical signals output from the transducers 121, and an A/D converter which coverts the analog signals output from the amplifier into digital signals. The signal collection unit 140 may include a field programmable gate array (FPGA) chip. The digital signals output from the signal collection unit 140 are stored into a storage unit 152 in the computer 150. The signal collection unit 140 is also referred to as a data acquisition system (DAS). In this specification, an electrical signal is a concept that covers both analog and digital signals. The signal collection unit 140 may be connected to a light detection sensor attached to the light emission part of the light irradiation unit 110, and may be triggered to start processing in synchronization with the emission of light from the light irradiation unit 110. The signal collection unit 140 may be triggered to start the processing in synchronization with an instruction given by using a freeze button.

(Computer 150)

The computer 150 serving as a display control unit includes an arithmetic unit 151, the storage unit 152, and a control unit 153. The functions of the respective components will be described in conjunction with the description of a processing flow.

A unit that performs arithmetic functions as the arithmetic unit 151 may include processors such as a central processing unit (CPU) and a graphics processing unit (GPU), or an arithmetic circuit such as an FPGA chip. Such units may not only include a single processor or arithmetic circuit, but include a plurality of processors or arithmetic circuits. The arithmetic unit 151 may receive various parameters such as the sound speed of the subject 100 and the configuration of the holding unit 200 from the input unit 170, and process received signals.

The storage unit 152 may include a non-transitory storage medium such as a read-only memory (ROM), a magnetic disk, and a flash memory. The storage unit 152 may be a volatile medium such as a random access memory (RAM). Programs are stored in a non-transitory storage medium. The storage unit 152 may not only include a single storage medium but include a plurality of storage media.

The storage unit 152 can store image data representing a photoacoustic image generated by the arithmetic unit 151 by a method to be described below.

The control unit 153 includes an arithmetic element such as a CPU. The control unit 153 controls the operation of the components of the photoacoustic apparatus. The control unit 153 may receive instruction signals of various operations, such as a start of measurement, from the input unit 170 and control the components of the photoacoustic apparatus. The control unit 153 reads program code stored in the storage unit 152 and controls the operation of the components of the photoacoustic apparatus.

The computer 150 may be a work station of dedicated design. The components of the computer 150 may be made of respective different pieces of hardware. At least some of the components of the computer 150 may be made of a single piece of hardware.

Figure 7:
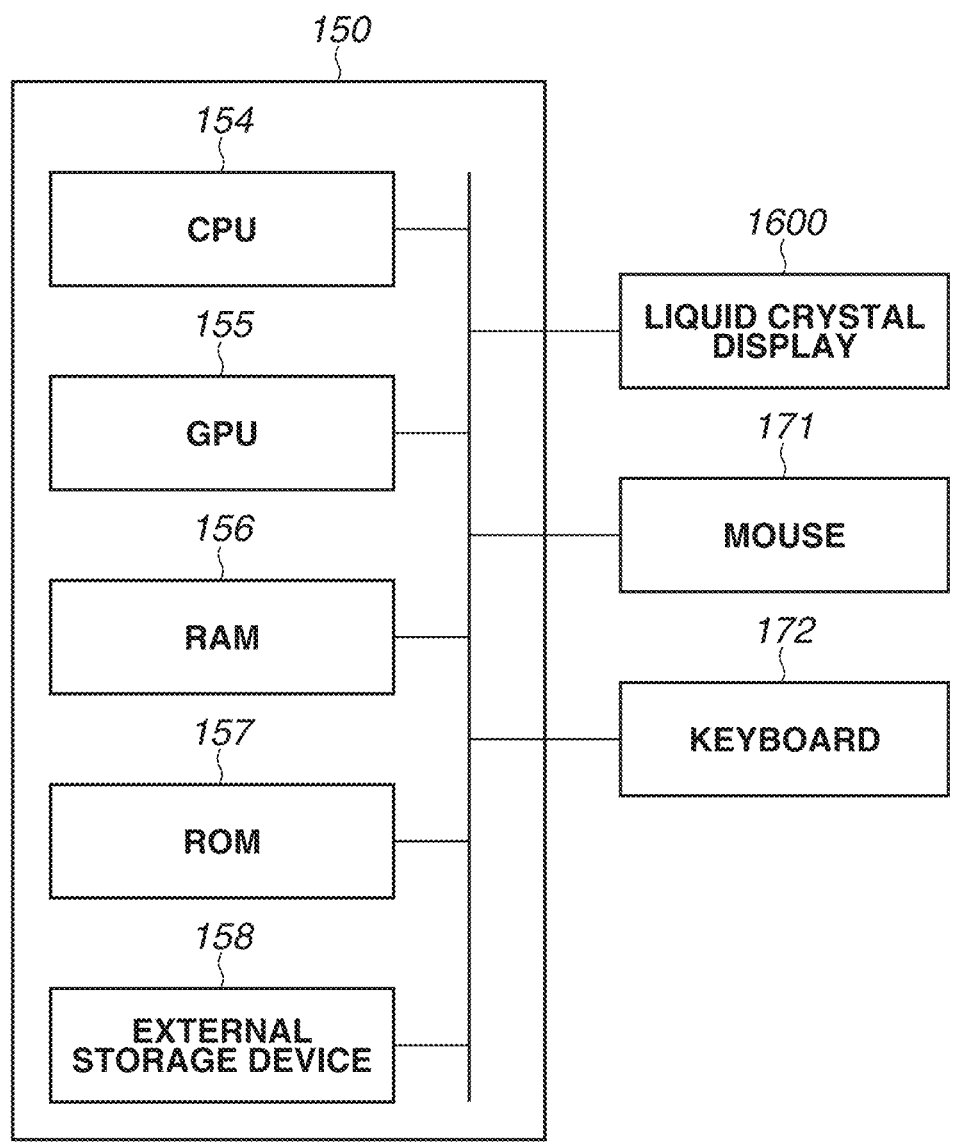
FIG. 7 is a block diagram illustrating a computer and its peripheral components according to the first exemplary embodiment.

FIG. 7 illustrates a specific configuration example of the computer 150 according to the present exemplary embodiment. The computer 150 according to the present exemplary embodiment includes a CPU 154, a GPU 155, a RAM 156, a ROM 157, and an external storage device 158. The computer 150 is connected with a liquid crystal display 1600 serving as the display unit 160, and a mouse 171 and a keyboard 172 serving as the input unit 170.

The computer 150 and the plurality of transducers 121 may be configured and provided as accommodated in a common housing. A computer accommodated in the housing may perform part of the signal processing while a computer provided outside the housing performs the rest of the signal processing. In such a case, the computers provided inside and outside the housing may be referred to collectively as the computer 150 according to the present exemplary embodiment. In other words, the pieces of hardware constituting the computer 150 do not need to be accommodated in a single housing.

(Display Unit 160)

The display unit 160 is a display such as a liquid crystal display, an organic electroluminescence (EL) field emission display (FED), a glass type display, and a head mounted display. The display unit 160 is a device that displays an image and a numerical value at a specific position based on volume data obtained by the computer 150. The display unit 160 may display an image based on image data and a GUI for operating the photoacoustic apparatus. In displaying subject information, the display unit 160 or the computer 150 may perform imaging processing (adjustment of brightness values) before display. The display unit 160 may be provided separately from the photoacoustic apparatus. The computer 150 can transmit photoacoustic image data to the display unit 160 in a wired or wireless manner.

(Input Unit 170)

A user-operable operation console including a mouse and a keyboard may be used as the input unit 170. The display unit 160 may include a touch panel, and the display unit 160 may be used as the input unit 170.

The input unit 170 may be configured such that information about a position and depth desired to be observed can be input. As for an input method, numerical values may be input. Information may be input by operating a slider bar. The image displayed on the display unit 160 may be updated according to the input information. In such a manner, the user can set appropriate parameters by checking the image generated with the parameters determined by his/her own operations.

The components of the photoacoustic apparatus may be configured as respective different apparatuses or as one integrated apparatus. At least some of the components of the photoacoustic apparatus may be configured as one integrated apparatus.

Information is transmitted and received between the components of the photoacoustic apparatus in a wired or wireless manner.

(Subject 100)

The subject 100, though not a component of the photoacoustic apparatus, will be described below. The photoacoustic apparatus according to the present exemplary embodiment can be used for the purposes of diagnosis of malignant tumors and vascular diseases of a human or an animal and follow-up of chemotherapy. The subject 100 can thus be a diagnostic part of a living body. Specific examples include the breast, organs, blood vessel network, head, neck, abdomen, and extremities including fingers and toes of a human body or an animal. For example, if the measurement object is a human body, oxyhemoglobin, deoxyhemoglobin, blood vessels containing much of these, or new blood vessels formed near a tumor may serve as the optical absorber. Plaques on a carotid wall may serve as the optical absorber. Dye such as methylene blue (MB) or indocyanine green (ICG), fine particles of gold, or externally-introduced substances formed by aggregating or chemically modifying the same may be used as the optical absorber.

Next, an image display method including information processing according to the present exemplary embodiment will be described with reference to FIG. 8. The following steps are performed by the computer 150 controlling the operation of the components of the photoacoustic apparatus.

(S100: Step of Setting Control Parameters)

In step S100, the user specifies, by using the input unit 170, control parameters needed to obtain subject information. The control parameters include an irradiation condition (including a repetition frequency and a wavelength) of the light irradiation unit 110 and a position of the probe 180. The computer 150 sets the control parameters determined based on the user's instructions.

(S200: Step of Moving Probe to Specified Position)

In step S200, the control unit 153 causes the driving unit 130 to move the probe 180 to the specified position based on the control parameters specified in step S100. If imaging at a plurality of positions is specified in step S100, the driving unit 130 initially moves the probe 180 to the first specified position. The driving unit 130 may move the probe 180 to a previously-programmed position when a start instruction for measurement is given. In the case of a handheld probe, the user may grip and move the probe 180 to a desired position.

(S300: Step of Irradiating Subject with Light)

In step S300, the light irradiation unit 110 irradiates the subject 100 with light based on the control parameters specified in step S100.

The subject 100 is irradiated with the light occurring from the light source 111, which is pulsed light, via the optical system 112. The pulsed light is absorbed inside the subject 100, and photoacoustic waves occur due to the photoacoustic effect. The light irradiation unit 110 transmits a synchronization signal to the signal collection unit 140 along with the transmission of the pulsed light.

(S400: Step of Receiving Photoacoustic Waves)

In step S400, the signal collection unit 140 receives the synchronization signal transmitted from the light irradiation unit 110 and starts an operation for signal acquisition. More specifically, the signal collection unit 140 generates and outputs amplified digital electrical signals to the computer 150 by performing amplification and A/D conversion on the analog electrical signals derived from acoustic waves, output from the reception unit 120. The computer 150 stores the signals transmitted from the signal collection unit 140 into the storage unit 152. If imaging at a plurality of scanning positions is specified in step S100, steps S200 to S400 are repeated for the specified scanning positions, whereby the irradiation with the pulsed light and the generation of digital signals derived from acoustic waves are repeated.

In the present exemplary embodiment, to obtain a spatial distribution of oxygen-saturation in step S500 to be described below, steps S300 and S400 are performed with a plurality of respective different wavelengths of light. The subject 100 may be either irradiated with each of the plurality of wavelengths of light in a time division manner or simultaneously irradiated with the plurality of wavelengths of light as long as the signals corresponding to the respective plurality of wavelengths can be individually obtained.

(S500: Step of Generating Photoacoustic Image Data)

In step S500, the arithmetic unit 151 in the computer 150 serving as a first acquisition unit generates and stores photoacoustic image data into the storage unit 152 based on signal data stored in the storage unit 152. Any technique may be used as a reconstruction algorithm for converting the signal data into photoacoustic image data which is a spatial distribution. Examples of the technique include time-domain back-projection, Fourier-domain back-projection, and model-based (repetitive calculation) methods. Examples of the time-domain back-projection method include universal back-projection (UBP), filtered back-projection (FBP), and delay-and-sum methods. For example, as a reconstruction technique for obtaining a spatial distribution of generated sound pressure (initial sound pressure) of acoustic waves as the photoacoustic image data, the arithmetic unit 151 may use a UBP method expressed by Eq. (1):

$$p_0(r_0) = \frac{\sum_i^N b\left(r_i, t = \frac{|r_i - r_0|}{c}\right) \cdot \Delta\Omega_i}{\sum_i^N \Delta\Omega_i} \quad (1)$$

$$b(r, t) = 2p(r, t) - 2t \frac{\partial p(r, t)}{\partial t}$$

Here, $r_0$ is a position vector representing the position to be reconstructed (also referred to as a reconstruction position or a position of interest), $p_0(r_0, t)$ is the initial sound pressure at the position to be reconstructed, and c represents the sound speed in the propagation path. $\Delta\Omega_i$ represents the solid angle of an ith transducer 121 from the position to be reconstructed, and N represents the number of transducers 121 used for reconstruction. Eq. (1) shows that differential processing is performed on reception signals $p(r_i, t)$, and the resultants are weighted with the respective solid angles for phase-regulated addition (back-projection). In Eq. (1), t is time (propagation time) for which photoacoustic waves propagate along a sound line connecting the position of interest and the transducer 121. Additional arithmetic processing may be applied to the calculation of $b(r_i, t)$. Examples of the additional arithmetic processing include frequency filtering (low-pass, high-pass, and band-pass filtering), deconvolution, envelope detection, and wavelet filtering.

The arithmetic unit 151 may calculate a light fluence distribution, in the subject 100, of the light with which the subject 100 is irradiated, and divide the initial sound pressure distribution by the light fluence distribution to obtain absorption coefficient distribution information. In such a case, the absorption coefficient distribution information may be obtained as photoacoustic image data. The computer 150 can calculate a spatial distribution of light fluence in the subject 100 by a method for numerically solving a transport equation or diffusion equation expressing the behavior of light energy in a light-absorbing and -diffusing medium. A finite element method, a difference method, or the Monte Carlo method may be used as a method for numerical solution. For example, the computer 150 may calculate the spatial distribution of light fluence in the subject 100 by solving the light diffusion equation expressed by Eq. (2):

$$\frac{1}{c}\frac{\partial}{\partial t}\Phi(r, t) = -\mu_a \Phi(r, t) + \nabla \cdot (D\nabla\Phi(r, t)) + S(r, t), \quad \text{Eq. (2)}$$

where D is a diffusion coefficient, $\mu_a$ is an absorption coefficient, S is the incident intensity of the irradiation light, $\Phi$ is light fluence of light to arrive, r is a position, and t is time.

In the present step, the arithmetic unit 151 can obtain absorption coefficient distribution information corresponding to each of the plurality of wavelengths of light. The arithmetic unit 151 may then obtain spatial distribution information (spectral information) about the concentrations of substances constituting the subject 100 as photoacoustic image data based on the absorption coefficient distribution information corresponding to the respective plurality of wavelengths of light. In other words, the arithmetic unit 151 may obtain spectral information by using the signal data corresponding to the plurality of wavelengths of light. In the present exemplary embodiment, photoacoustic image data indicating a spatial distribution of oxygen-saturation is obtained as the spectral information.

In the present exemplary embodiment, the spatial distribution of oxygen-saturation is described to be obtained based on the absorption coefficient distribution information corresponding to each of the plurality of wavelengths of light. However, any method may be used as long as a spatial distribution of an oxygenation index can be obtained. For example, the results of the calculations of ratios between the initial sound pressure distributions corresponding to the respective plurality of wavelengths of light are also information indicating the degree of oxygenation, and are included in the oxygenation index. Information identifying the degree of oxygenation in grades (for example, information classifying the magnitude of oxygen-saturation under three classifications high, medium, and low) is also included in the oxygenation index. For example, such information that an oxygen-saturation of 0% or more and less than 70% is classified to be "low", 70% or more and less than 90% "medium", and 90% or more and not more than 100% "high" may be obtained as the information identifying the degree of oxygenation in grades. Information indicating a spatial distribution of an oxygenation index may be obtained by using modalities other than the photoacoustic apparatus.

(S600: Step of Displaying Image Based on Photoacoustic Image Data)

Figure 9A:
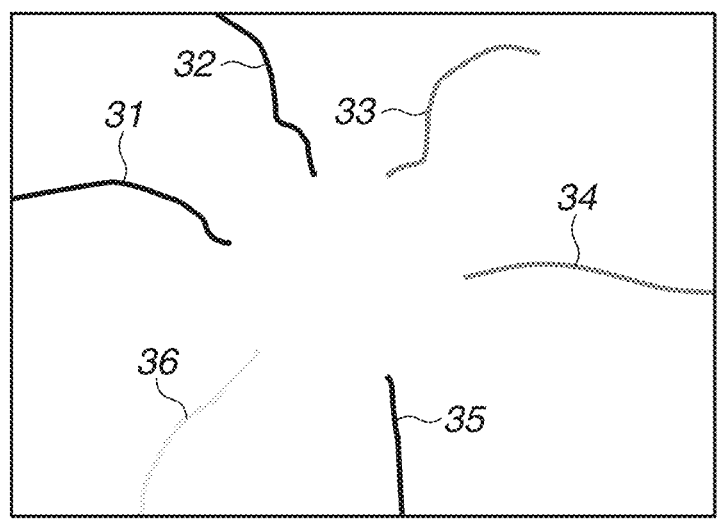
FIGS. 9A and 9B are schematic diagrams illustrating an example of designating a region of interest according to the first exemplary embodiment.

In step S600, the computer 150 serving as the display control unit generates and displays an image on the display unit 160 based on the photoacoustic image data obtained in step S500. In the present exemplary embodiment, as illustrated in FIG. 9A, the computer 150 generates and displays an image indicating the spatial distribution of oxygen-saturation on the display unit 160 based on the photoacoustic image data. The image in FIG. 9A is similar to that in FIG. 3B. If the photoacoustic image data expresses a three-dimensional spatial distribution, the computer 150 may display an image on the display unit 160 by rendering the photoacoustic image data by a conventional technique. Any conventional technique may be use for the rendering. Examples of the conventional technique include maximum intensity projection (MIP), minimum intensity projection (MinIP), ray sum, average intensity projection, medium intensity projection, volume rendering, and surface rendering. The photoacoustic apparatus according to the present exemplary embodiment may be configured such that the user can select a rendering technique by using the input unit 170. If the direction of arrangement of reconstruction voxels does not coincide with the line-of-sight direction (projection direction), the reconstruction voxels may be divided and rendering processing may be performed on the interpolated volume data. An image may be generated and displayed by a parallel projection method with a single line-of-sight direction, or a perspective projection method in which directions extending radially from a point are projected on the line-of-sight direction (projection direction).

The user may issue instructions to change the region desired to be expressed as an image and sequentially switch display images by operating a wheel of the mouse 171 serving as the input unit 170.

(S700: Step of Obtaining Information Indicating Region of Interest)

Figure 9B:
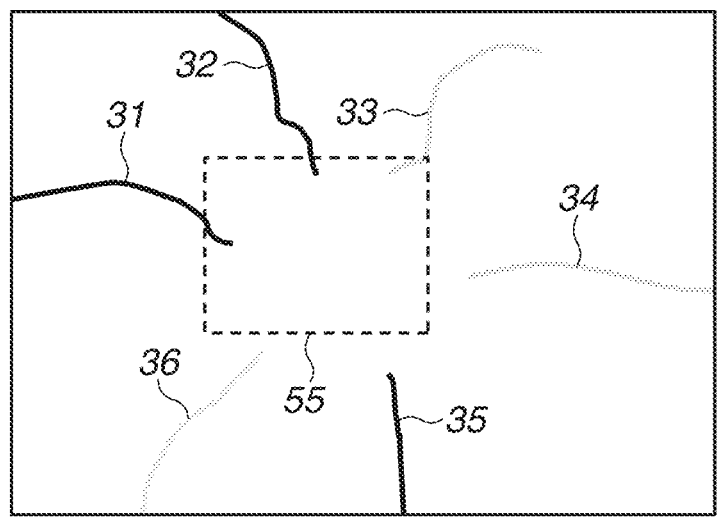

In step S700, as illustrated in FIG. 9B, the user designates a region of interest 55 on the image based on the photoacoustic image data by using the input unit 170. The input unit 170 outputs information indicating the region of interest 55 to the computer 150, and the computer 150 receives the information. In other words, the computer 150 serving as a second acquisition unit obtains the information indicating the region of interest 55 determined based on the user's instructions. The information indicating the region of interest 55 may be any information as long as the region of interest 55 can be identified from the information. Examples of the information indicating the region of interest 55 include information indicating the position (coordinates) of the outer periphery of the region of interest 55, and information indicating the position (coordinates) of a voxel group (or pixel group) constituting the region of interest 55.

In the present exemplary embodiment, the region of interest 55 has been described to be designated on the display image based on the photoacoustic image data, by the user. However, the region of interest 55 may be designated by any method. For example, as will be described below, the region of interest 55 may be designated in a display image (medical image) based on image data obtained by modality apparatuses other than the photoacoustic apparatus (such as an ultrasound diagnostic apparatus, a magnetic resonance imaging (MRI) apparatus, an X-ray computed tomography (CT) apparatus, or a positron emission tomography (PET) apparatus). The computer 150 may determine the region of interest 55 by analyzing image data.

(S800: Step of Displaying Image Indicating Condition of Tissue Included in Region of Interest)

Figure 10:
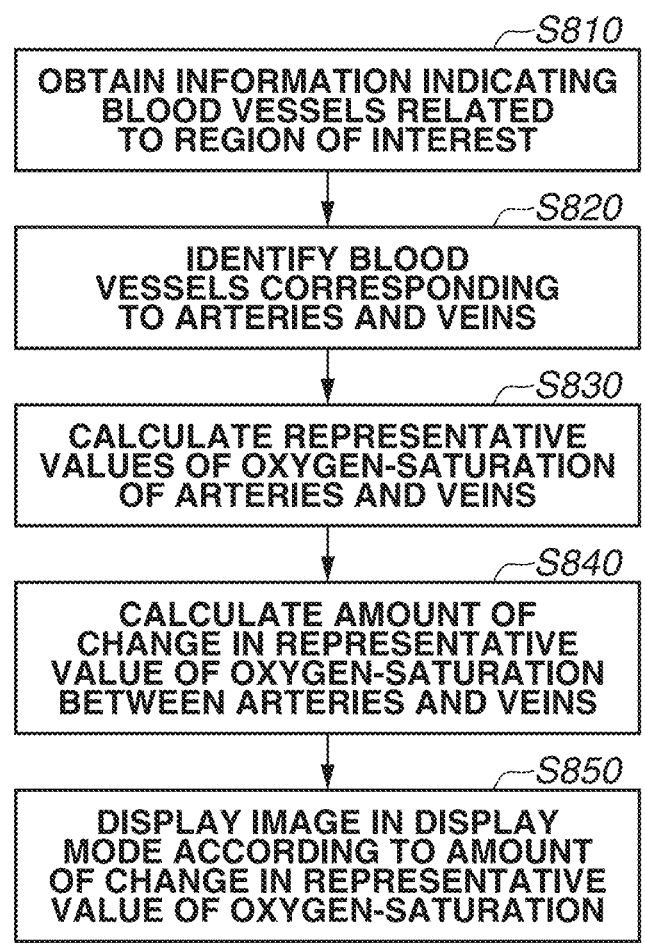
FIG. 10 is a detailed flowchart of the image display method according to the first exemplary embodiment.

In step S800, the computer 150 estimates a condition of a tissue included in the region of interest 55 set in step S700, based on the spatial distribution of oxygen-saturation obtained in step S600. The computer 150 serving as the display control unit then displays an image on the display unit 160 in a display mode according to the condition of the tissue included in the region of interest 55. Specific processing of the present step is described below with reference to FIG. 10.

(S810: Step of Obtaining Information Indicating Blood Vessels Related to Region of Interest)

In step S810, the computer 150 serving as a third acquisition unit obtains information indicating blood vessels related to the region of interest 55. Here, information indicating a blood vessel may be any information as long as the blood vessel can be identified from the information. Examples of the information indicating a blood vessel include information indicating the position (coordinates) of the outer periphery of the blood vessel and information indicating the position (coordinates) of a voxel group (pixel group) constituting the blood vessel.

The computer 150 may identify the blood vessels related to the region of interest 55 based on the information indicating the region of interest 55. For example, in the case of FIG. 9B, the computer 150 may segment the blood vessels related to the region of interest 55 by analyzing the photoacoustic image data. The computer 150 can identify images overlapping with the region of interest 55, among images having spatially continuous image values, as blood vessels related to the region of interest by analyzing the photoacoustic image data. More specifically, the computer 150 can identify the blood vessels 31, 32, and 33 overlapping with the region of interest 55 as the blood vessels related to the region of interest 55. While the computer 150 determines here the images having spatially continuous image values to be the images of blood vessels, other conventional image processing may be applied as long as the images of blood vessels can be determined. For example, the computer 150 may determine, as an image of a blood vessel, an image in which the oxygen-saturation is included in a numerical range of high likelihood of being a blood vessel in the spatial distribution of oxygen-saturation. The computer 150 may determine, as an image of a blood vessel, a region in which the oxygen-saturation is 0% or more and not more than 100%. The computer 150 may determine, as an image of a blood vessel, a region in which the oxygen-saturation is 50% or more and not more than 100%.

Figure 11A:
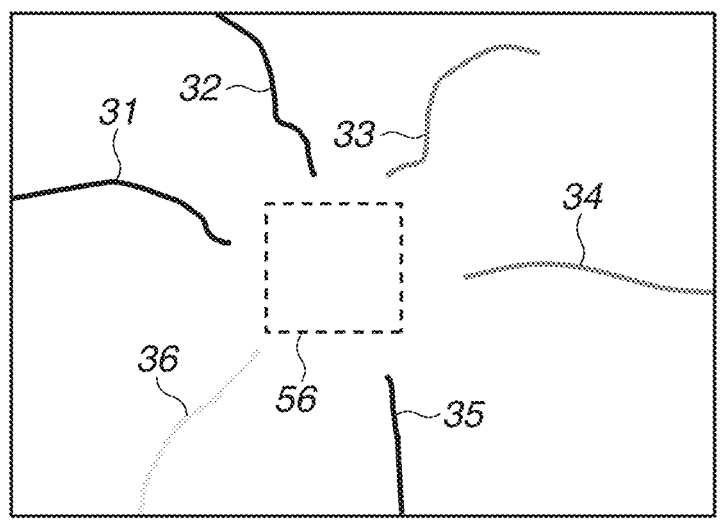
FIGS. 11A and 11B are schematic diagrams illustrating another example of designating a region of interest according to the first exemplary embodiment.
Figure 11B:
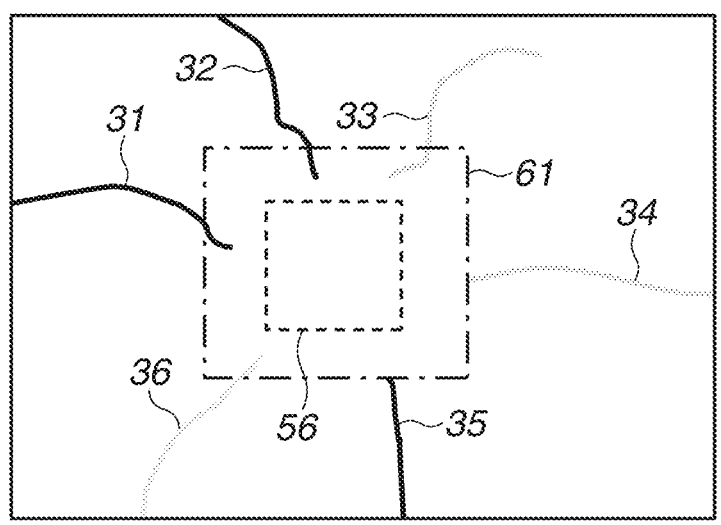

Suppose, for example, that a region of interest 56 that does not overlap with any of the images of the blood vessels 31 to 36 is set as illustrated in FIG. 11A. The computer 150 defines a region 61 (dot-dashed line) having a predetermined relationship with the region of interest 56 as illustrated in FIG. 11B. The computer 150 may then identify images overlapping with the region 61, among the images having spatially continuous image values, as blood vessels related to the region of interest 56 by analyzing the photoacoustic image data. In such a case, the computer 150 determines the blood vessels 31, 32, 33, and 36 to be blood vessels related to the region of interest 56.

Here, the region 61 formed by enlarging the designated region of interest 56 at a predetermined enlargement ratio is defined as the region having a predetermined relationship with the region of interest 56. However, a region uniquely determined when the region of interest 56 is designated, like a region formed by enlarging the designated region of interest 56 by a predetermined distance, may be defined as the region having a predetermined relationship with the region of interest 56. The user may specify information indicating the predetermined relationship (such as a ratio of enlargement and a distance of enlargement) by using the input unit 170.

The computer 150 may calculate whether there is an image overlapping with the region of interest 56 designated by the user among the images included in the photoacoustic image data. If the calculation shows that there is no image overlapping with the region of interest 56, the computer 150 may determine a region within a predetermined distance around the region of interest 56 and determine images overlapping with the region as the images of blood vessels. If the calculation shows that there is an image or images overlapping with the region of interest 56, the computer 150 may determine the images as the images of blood vessels.

In the following steps, a case where the region of interest 55 in FIG. 9B is designated will be described.

(S820: Step of Identifying Blood Vessels Corresponding to Arteries and Veins)

In step S820, the computer 150 identifies arteries and veins among the images of the blood vessels identified in step S810. In other words, the computer 150 discriminates images corresponding to arteries from ones corresponding to veins.

Typically, arteries have an oxygen-saturation of near 100%, and veins have an oxygen-saturation lower than that of arteries. For example, the computer 150 may set a threshold for the spatial distribution of oxygen-saturation, determine an image of a blood vessel having an oxygen-saturation higher than the threshold as an image of an artery, and determine an image of a blood vessel having an oxygen-saturation lower than the threshold as an image of a vein. The threshold for discriminating arteries from veins may have a value of 80% or more and not more than 95%. The threshold may have a value of 85% or more and not more than 95%. The threshold may have a value of 90% or more and not more than 95%. If a threshold of 90% is set for the blood vessels 31, 32, and 33 related to the region of interest 55 in FIG. 9B, the computer 150 determines the blood vessels 31 and 32 having an oxygen-saturation of more than 90% as arteries, and the blood vessel 33 having an oxygen-saturation of less than 90% as a vein. The computer 150 may determine that the blood vessel having the oxygen saturation equal to the threshold value is an artery or a vein. The criterion for discriminating between an artery and a vein may be determined in advance or may be determined according to an instruction from the user. In the following steps, the blood vessels 31 and 32 will be described to be arteries and the blood vessel 33 a vein.

Suppose that information identifying the degree of oxygenation in grades as an oxygenation index is obtained. Suppose that information in which oxygen-saturations of 0% or more and less than 70% are classified as "low", 70% or more and less than 90% "medium", and 90% or more and not more than 100% "high" is obtained as the information identifying the degree of oxygenation in grades as an oxygenation index. In such a case, the computer 150 may determine an area classified as "high" to be an artery, and determine an area classified as "medium" or "low" to be a vein.

Arteries and veins may be discriminated in light of the fact that an artery and a vein run side by side. For example, the computer 150 may analyze the photoacoustic image data to identify two blood vessels running side by side, and determine either one of the blood vessels that has a higher oxygen-saturation, as an artery, and one having a lower oxygen-saturation, as a vein. The user may observe the display image of the photoacoustic image data and specify two blood vessels running side by side on the display image by using the input unit 170. The computer 150 may then compare the oxygen-saturations of the two specified blood vessels to determine an artery and a vein. The image data on which the user specifies two blood vessels may be image data obtained by a modality other than the photoacoustic apparatus.

The computer 150 may determine arteries and veins by analyzing the photoacoustic image data or image data obtained by a modality other than the photoacoustic apparatus, using prior anatomical information indicating typical positions of arteries and veins.

The computer 150 may determine whether a blood vessel related to the region of interest 55 is an artery or a vein by analyzing the direction of the blood flowing in the blood vessel based on Doppler image data. More specifically, the computer 150 may determine a blood vessel in which the blood flows toward the region of interest 55 as an artery, and a blood vessel in which the blood flows away from the region of interest 55 as a vein.

Arteries and veins may be discriminated in view of a difference in pulsation between the arteries and veins. For example, the computer 150 may obtain information indicating the pulsation of the blood vessels in the image data, and determine blood vessels of which the amplitude of pulsation is greater than a threshold, as arteries. The computer 150 can obtain the information indicating the amplitude of pulsation by obtaining a time series of images of the blood vessels related to the region of interest 55 and calculating temporal changes in the diameters of the blood vessels.

The user may designate, by using the input unit 170, at least either arteries or veins related to the region of interest 55 on the display image (medical image) of the photoacoustic image data or image data obtained by a modality other than the photoacoustic apparatus.

(S830: Step of Calculating Representative Values of Oxygen-Saturation of Arteries and Veins)

In step S830, the computer 150 serving as a determination unit calculates a representative value of the oxygen-saturation of the blood vessels 31 and 32 corresponding to arteries, identified in step S820. The computer 150 also calculates a representative value of the oxygen-saturation of the blood vessel 33 corresponding to a vein, identified in step S820. For example, the representative values include at least one of an average, a median, and a mode.

Suppose that an average is used as a representative value. In such a case, the computer 150 calculates the representative value of the oxygen-saturation of the blood vessels 31 and 32 corresponding to arteries to be 98%. The computer 150 calculates the representative value of the oxygen-saturation of the blood vessel 33 corresponding to a vein to be 70%.

The oxygen-saturation of a blood vessel can change with position. The computer 150 may therefore assume a representative value of oxygen-saturations at a plurality of positions in a blood vessel in question as the oxygen-saturation of the blood vessel. The computer 150 may calculate representative values of oxygen-saturation of blood vessels included in a region having a predetermined relationship with the region of interest 55.

The computer 150 may assign weights to the values of oxygen-saturation of respective blood vessels before calculating a representative value. For example, based on information indicating the region of interest 55 and information indicating the positions of the blood vessels, the computer 150 may calculate a representative value by assigning higher weights to blood vessels closer to the region of interest 55.

The user may then designate blood vessels related to the region of interest 55 by using the input unit 170. Here, the user may designate part of regions of blood vessels as the blood vessels related to the region of interest 55 on a medical image (image in which the blood vessels appear) displayed on the display unit 160. As described above, the oxygen-saturation of a blood vessel changes with position. The user may therefore designate a blood vessel region to be calculated. The computer 150 can obtain information indicating the blood vessels related to the region of interest 55 via the input unit 170. In such a case, the computer 150 can obtain the information indicating the blood vessels related to the region of interest 55 without using the information indicating the region of interest 55.

(S840: Step of Calculating Amount of Change in Representative Value of Oxygen-Saturation Between Arteries and Veins)

In step S840, the computer 150 obtains information indicating a change between the representative values of oxygen-saturation of the arteries and veins, calculated in step S830. The computer 150 can obtain information indicating a discrepancy in the representative value by calculating a difference or a ratio between the representative values. Calculation methods other than those of a difference and a ratio may be used as long as the amount of change in the representative value can be identified.

In the present exemplary embodiment, the amount of change in the representative value will be described to be calculated by calculating a difference between the representative values. More specifically, the computer 150 calculates a difference (28%) between the representative value (98%) of oxygen-saturation of the blood vessels 31 and 32 corresponding to arteries and the representative value (70%) of oxygen-saturation of the blood vessel 33 corresponding to a vein.

(S850: Step of Displaying Image in Display Mode According to Amount of Change in Representative Value of Oxygen-Saturation)

In step S850, the computer 150 determines the display mode according to a change in the representative value based on the information indicating a discrepancy in the representative value of oxygen-saturation between arteries and veins, obtained in step S840. The computer 150 then displays the image of the region of interest 55 on the display unit 160 in the determined display mode.

As described above, the computer 150 corresponds to the first acquisition unit, the second acquisition unit, the third acquisition unit, the determination unit, and the display control unit according to the present exemplary embodiment.

Figure 12:
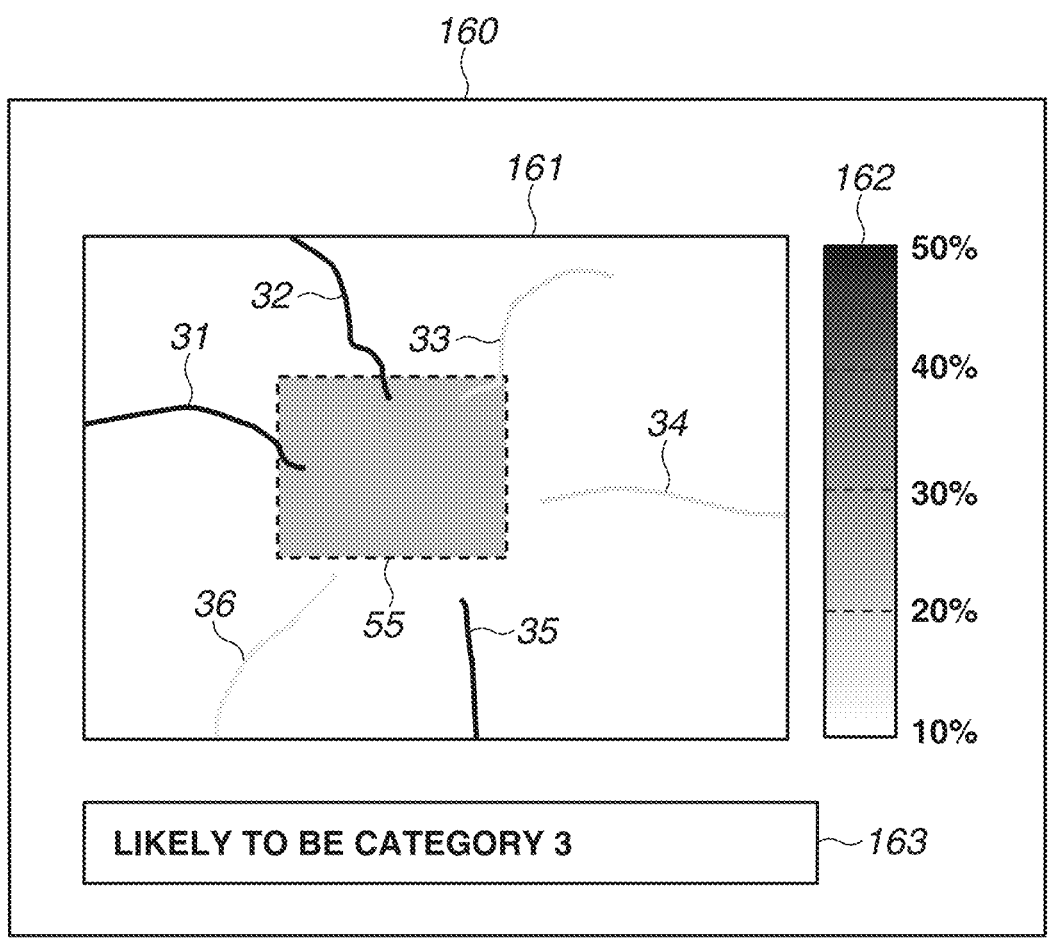
FIG. 12 is a schematic diagram illustrating a display example of a display unit according to the first exemplary embodiment.

FIG. 12 illustrates a display example of the display unit 160 according to the present exemplary embodiment. FIG. 12 illustrates a display example when a region of interest 55 is designated in an image 161 indicating a spatial distribution of oxygen-saturation. In the present exemplary embodiment, as illustrated in FIG. 12, the amount of change in the representative value is applied to a color scale 162 of the display color of the region of interest 55 to determine the display mode (display color) of the region of interest 55. On the color scale 162 used here, different colors are assigned to differences of 10% to 50% in the representative value. In FIG. 12, the difference in the representative value is 28%, and the image of the region of interest 55 is displayed in a display color corresponding to 28% on the color scale 162. Typically, it is conceivable that the higher the degree of drop from the oxygen-saturation of the arteries to that of the veins is, the higher the degree of malignancy (activity) of the tissue is. It is conceivable that the higher the degree of drop from the oxygen-saturation of the arteries to that of the veins is, the more likely the tissue is to be malignant. Such a display method can thus facilitate the comprehension of the condition (degree of malignancy or activity) of the tissue included in the region of interest 55. If the display color of the image of the region of interest 55 is changed as a display mode, the images of blood vessels overlapping with the colored region of interest 55 may drop in visibility. In such a case, the images of the blood vessels may be superimposed on the image of the region of interest 55 to suppress the drop in the visibility of the blood vessels. The display color of the images of the blood vessels or the image of the region of interest 55 may be determined such that the display color of the image of the region of interest 55 is not of the same type as the display color of the images of the blood vessels.

If information identifying the degree of oxygenation in grades is obtained as an oxygenation index (for example, if the degree of oxygenation is identified in three grades "high", "medium", and "low" as described above), the computer 150 may estimate the condition of the tissue from a combination of such pieces of information. More specifically, the computer 150 may estimate the condition of the tissue in the region of interest 55 according to a combination of the degree (high, medium, or low) of oxygenation of blood vessels for supplying blood to the tissue in the region of interest 55 and the degree (high, medium, or low) of oxygenation of blood vessels carrying blood flowing away from the tissue in the region of interest 55. The computer 150 may determine the display mode of the display image of the region of interest 55 according to the combination of the degree (high, medium, or low) of oxygenation of the blood vessels for supplying blood to the tissue in the region of interest 55 and the degree (high, medium, or low) of oxygenation of the blood vessels carrying blood flowing away from the tissue in the region of interest 55. For example, suppose that among all combinations, the combination is such that the degree of oxygenation of the blood vessels for supplying blood to the tissue in the region of interest 55 is "high" and the degree of oxygenation of the blood vessels carrying blood flowing away from the tissue in the region of interest 55 is "low". In such a case, the computer 150 may estimate that the tissue is most likely to be malignant. In other words, the computer 150 may estimate that the lower the degree of oxygenation of the blood vessels carrying blood flowing away from the tissue in the region of interest 55 is than that of the blood vessels for supplying blood to the tissue in the region of interest 55, the more likely the tissue is to be malignant. Alternatively, the computer 150 may estimate that the lower the degree of oxygenation of the blood vessels carrying blood flowing away from the tissue in the region of interest 55 is than that of the blood vessels for supplying blood to the tissue in the region of interest 55, the higher the degree of malignancy of the tissue is.

Any display mode may be used as long as the condition of the tissue included in the region of interest 55 can be comprehended. For example, the computer 150 may change, according to the condition of the tissue (the amount of change in the representative value), at least one of the following: the presence or absence of blinking of the image of the region of interest 55, a blinking pattern of the image of the region of interest 55, the line type of the outer periphery indicating the region of interest 55, and the hue, brightness, and saturation of the image of the region of interest 55.

The computer 150 may display an image expressing the condition of the tissue included in the region of interest 55 by text on the display unit 160. The image expressing the condition of the tissue included in the region of interest 55 by text may be displayed on the image of the region of interest 55.

For example, if the present exemplary embodiment is applied to aid the diagnosis of breast cancer, the computer 150 may assign the amount of change in the representative value to the categories of Breast Imaging Reporting and Data System (BI-RADS), and display a text image indicating the category of the tissue included in the region of interest 55 on the display unit 160. For example, if the difference in the representative value is 0% to 10%, the computer 150 determines category 1 as a candidate. If the difference in the representative value is 10% to 20%, the computer 150 determines category 2 as a candidate. If the difference in the representative value is 20% to 30%, the computer 150 determines category 3 as a candidate. If the difference in the representative value is 30% to 40%, the computer 150 determines category 4 as a candidate. If the difference in the representative value is 40% to 50%, the computer 150 determines category 5 as a candidate. Then, an image indicating the candidate of the category determined by the computer 150 may be displayed on the display unit

160. In FIG. 12, the difference in the representative value is 28%, and the computer 150 displays a text image 163 indicating that the tissue included in the region of interest 55 is likely to be category 3.

In the present exemplary embodiment, the condition of the tissue is described to be estimated by using the oxygenation index. However, the condition of the tissue may be estimated in consideration of an index other than the oxygenation index as well.

As described above, FIG. 12 illustrates a composite image of the image indicating the spatial distribution of oxygen-saturation and the image indicating the condition of the tissue included in the region of interest 55. As employed herein, a composition image refers to a superimposed image or juxtaposed images of the image indicating the spatial distribution of oxygen-saturation and the image indicating the condition of the tissue included in the region of interest 55.

The display by the image processing method according to the present exemplary embodiment enables the user to easily find out the condition (degree of malignancy or activity) of the tissue included in the region of interest 55.

In the present exemplary embodiment, the photoacoustic apparatus which is a modality is described to generate image data, and the image processing method according to the present exemplary embodiment is described to be applied to the generated image data. However, an image processing apparatus different from the modality may perform the image processing method according to the present exemplary embodiment. In such a case, the image processing apparatus reads and obtains image data previously generated by the modality from a storage unit such as a picture archiving and communication system (PACS), and applies the image processing according to the present exemplary embodiment to the image data. The image processing method according to the present exemplary embodiment can thus be applied to previously generated image data.

In the present exemplary embodiment, the photoacoustic apparatus is described as an example of a modality for obtaining image data indicating a spatial distribution of an oxygenation index. However, other imaging apparatuses may be used as long as image data indicating a spatial distribution of an oxygenation index can be obtained. For example, the present exemplary embodiment is applicable to an imaging apparatus that can obtain image data indicating a spatial distribution of oxygen-saturation or another oxygenation index, such as a diffusion optical tomography (DOT) apparatus and an acousto-optical tomography (AOT) apparatus. The DOT apparatus is an imaging apparatus that obtains image data based on detection signals of diffused light having propagated through the subject. The AOT apparatus is an imaging apparatus that modulates the frequency of light which propagates through the subject, by ultrasonic waves, and that obtains image data based on detection signals of the modulated light.

In the present exemplary embodiment, a mode for estimating the condition of the tissue included in the region of interest 55 based on the oxygenation indexes of blood vessels (arteries) for supplying blood to the region of interest 55 and the oxygenation indexes of blood vessels (veins) carrying blood flowing away from the region of interest 55 has been described. However, the condition of the tissue can be estimated without a distinction between arteries and veins. For example, the computer 150 may calculate variations in the oxygenation indexes of the blood vessels related to the region of interest 55, and estimate the condition of the tissue based on the variations in the oxygenation indexes.

Large variations in the oxygenation indexes of the blood vessels related to the region of interest 55 mean that a discrepancy between the oxygenation index of the artery and the oxygenation index of the vein is large. The computer 150 may therefore estimate the larger the variations in the oxygenation indexes are, the more likely that the tissue is to be malignant. The computer 150 may estimate that the larger the variations in the oxygenation indexes are, the higher the degree of malignancy of the tissue is to be. The computer 150 may handle information indicating variations in the oxygenation indexes as information indicating a discrepancy in the oxygenation indexes of the blood vessels related to the region of interest 55. Even in such a case, the information processing method described in the present exemplary embodiment can be applied.

A second exemplary embodiment describes a mode in which a region of interest is designated in a display image based on image data obtained by a modality different from the photoacoustic apparatus. In particular, in the second exemplary embodiment, an example where an ultrasound diagnostic apparatus is applied as a modality different from the photoacoustic apparatus will be described. In the second exemplary embodiment, a photoacoustic apparatus similar to that described in the first exemplary embodiment is used. Components described above are designated by the same reference numerals, and a detailed description thereof will be omitted.

In the present exemplary embodiment, the transducers 121 of the probe 180 output electrical signals (also referred to as ultrasonic signals) by transmitting ultrasonic waves based on control signals from the control unit 153 and receiving reflected waves of the transmitted ultrasonic waves. Transducers for transmitting ultrasonic waves and transducers for receiving acoustic waves may be separately provided. Transducers for transmitting ultrasonic waves and transducers for receiving acoustic waves may be made of the same transducers. Transducers for transmitting and receiving ultrasonic waves and transducers for receiving photoacoustic waves may be separately provided. Transducers for transmitting and receiving ultrasonic waves and transducers for receiving photoacoustic waves may be made of the same transducers.

Figure 13:
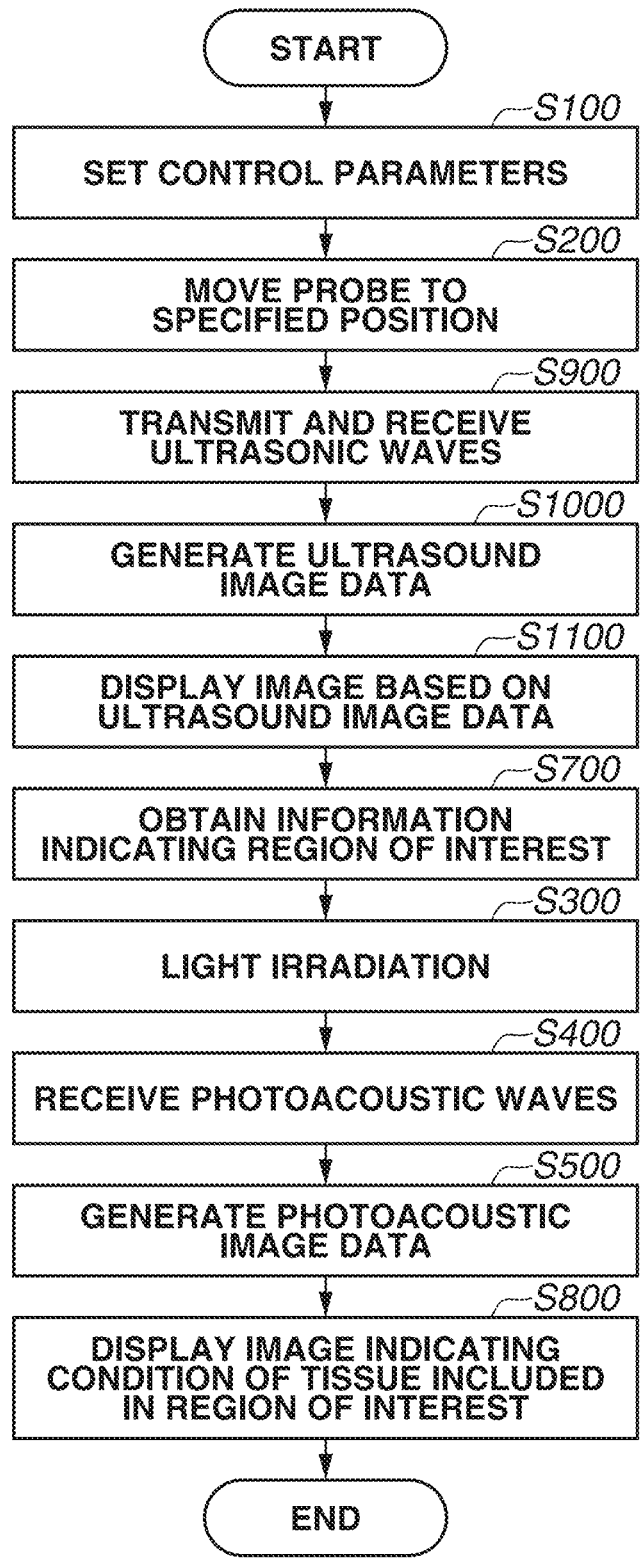
FIG. 13 is a flowchart of an image display method according to a second exemplary embodiment.

An image display method including image processing according to the present exemplary embodiment will be described with reference to FIG. 13. The following steps are performed by the computer 150 controlling the operation of the components of the photoacoustic apparatus. Steps similar to those illustrated in FIG. 8 are designated by the same reference numerals, and a detailed description thereof will be omitted.

Steps S100 and S200 are initially performed to locate the probe 180 at a specified position.

(S900: Step of Transmitting and Receiving Ultrasonic Waves)

In step S900, the probe 180 outputs ultrasonic signals by transmitting and receiving ultrasonic waves to/from the subject 100. The signal collection unit 140 performs A/D conversion processing on the ultrasonic signals, and transmits the processed ultrasonic signals to the computer 150. The ultrasonic signals which are digital signals are stored into the storage unit 152.

To generate three-dimensional ultrasound image data in step S1000 to be described below, the probe 180 may transmits and receives ultrasonic plane waves in a plurality of directions to collect ultrasonic signals. If transmission and reception at a plurality of positions are needed for the generation of three-dimensional ultrasound image data, the probe 180 may repeat transmission and reception at a plurality of positions to collect ultrasonic signals by repeating steps S200 and S900.

(S1000: Step of Generating Ultrasound Image Data)

In step S1000, the computer 150 generates ultrasound image data by performing reconstruction processing such as delay-and-sum processing on the ultrasonic signals. After the generation of the ultrasound image data, the computer 150 may delete the ultrasonic signals stored in the storage unit 152. As the ultrasound image data, the computer 150 can obtain, for example, at least one of the following: B-mode image data, Doppler image data, and elastography image data. The present exemplary embodiment describes the case of generating B-mode image data as the ultrasound image data. B-mode image data is image data derived from ultrasonic waves (echoes) reflected at interfaces of different tissues. B-mode image data includes image data indicating a tumor.

The present step may be performed after the collection of all the ultrasonic signals. The present step may be repeated each time ultrasonic waves are transmitted and received. Steps S900 and S1000 may use any method as long as ultrasound image data can be generated by the transmission and reception of ultrasonic waves.

In the present exemplary embodiment, the computer 150 generates ultrasound image data on the same region as the photoacoustic image data generated in step S500. However, the generation regions of the photoacoustic image data and the ultrasound image data do not need to be the same as long as the photoacoustic image data and the ultrasound image data on the region desired to be observed can be generated.

(S1100: Step of Displaying Image Based on Ultrasound Image Data)

In step S1100, the computer 150 generates and displays a B-mode image on the display unit 160 based on the ultrasound image data (B-mode image data) generated in step S1000. FIG. 14A illustrates an example of the B-mode image displayed on the display unit 160.

Figure 14B:
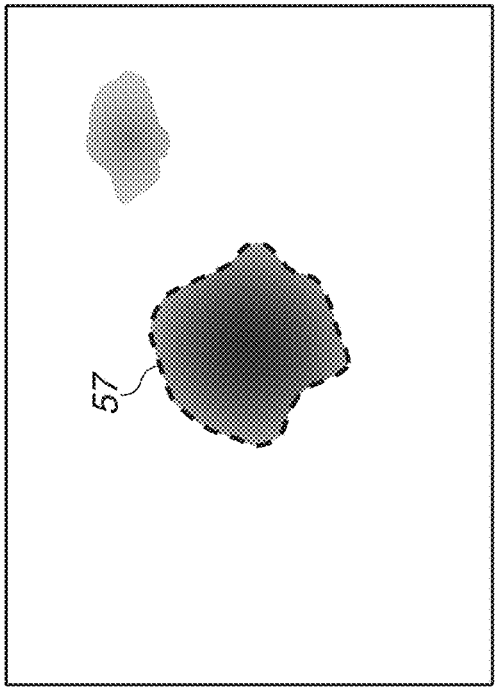
FIGS. 14A, 14B, 14C, and 14D are schematic diagrams illustrating an image processing method according to the second exemplary embodiment.

In step S700, as illustrated in FIG. 14B, the user designates a region of interest 57 in the B-mode image displayed on the display 160. As a result, the computer 150 obtains information indicating the region of interest 57.

In steps S300 to S500, the photoacoustic apparatus according to the present exemplary embodiment obtains photoacoustic image data indicating a spatial distribution of oxygen-saturation as described in the first exemplary embodiment. The present exemplary embodiment describes a case where the photoacoustic image data illustrated in FIG. 3B is obtained. The computer 150 may identify the positions of blood vessels related to the region of interest 57 before the acquisition of photoacoustic image data, and may selectively obtain image data indicating a spatial distribution of oxygen-saturation of the blood vessels related to the region of interest 57 based on such position information.

The photoacoustic apparatus according to the present exemplary embodiment may obtain the photoacoustic image data before the acquisition of the ultrasound image data. If the photoacoustic apparatus according to the present exemplary embodiment performs light irradiation and the reception of photoacoustic waves a plurality of times, the photoacoustic apparatus may perform the transmission and reception of ultrasonic waves in step S900 between one light irradiation operation and the next.

Figure 14D:
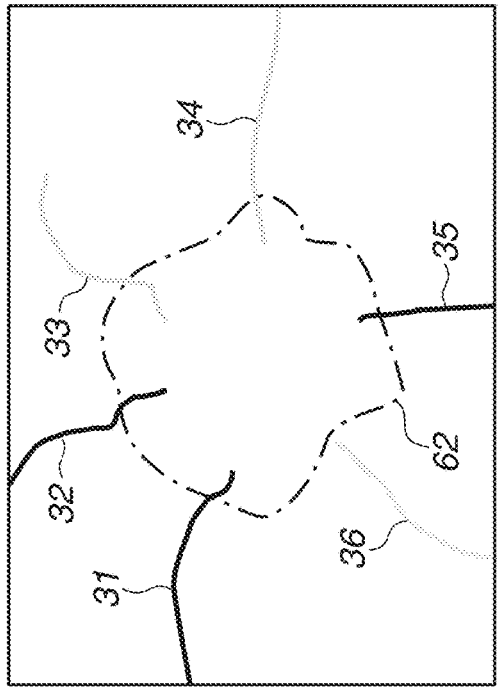
Figure 14A:
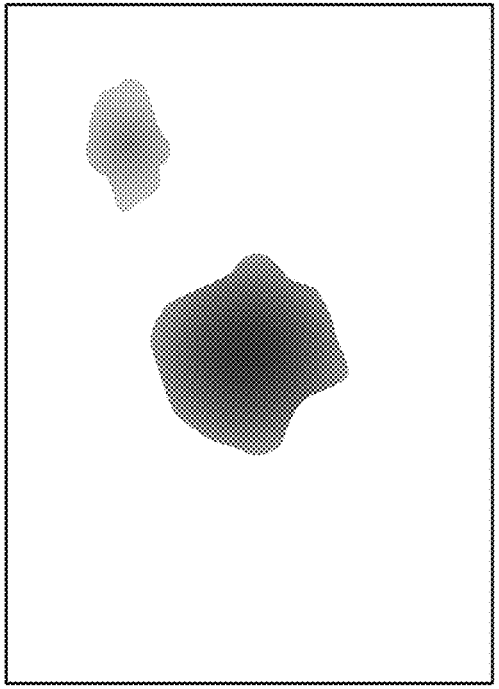
Figure 14C:
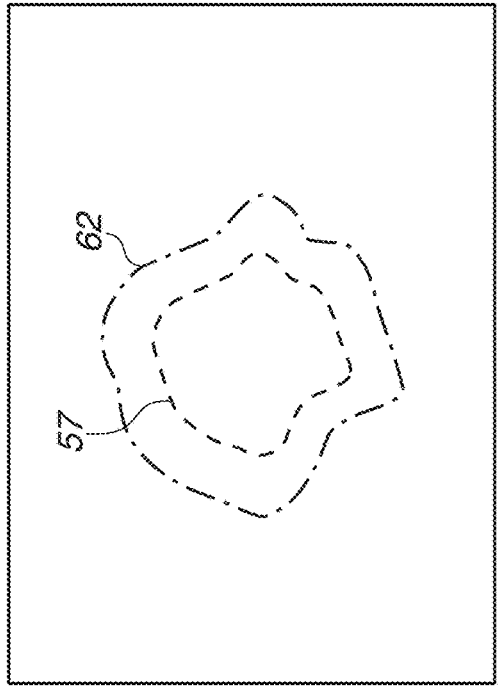

As described in the first exemplary embodiment, the computer 150 may determine the images of blood vessels overlapping with the region of interest 57 in the photoacoustic image data, as the images of the blood vessels related to the region of interest 57. In the present exemplary embodiment, as illustrated in FIG. 14C, the computer 150 defines a region 62 (dot-dashed line) by enlarging the region of interest 57 at a predetermined enlargement ratio, and determines the images of blood vessels overlapping with the region 62 in the photoacoustic image data as the images of the blood vessels related to the region of interest 57. As illustrated in FIG. 14D, the computer 150 determines the blood vessels 31, 32, 33, 34, and 35 overlapping with the region 62 in the photoacoustic image data as the images of the blood vessels related to the region of interest 57. If the coordinate system of the ultrasound image data does not correspond to that of the photoacoustic image data, the computer 150 can identify the photoacoustic images of the blood vessels overlapping with the region 62 by performing conversion processing on the coordinate systems.

The computer 150 discriminates the blood vessels related to the region of interest 57 between arteries and veins by the method described in the first exemplary embodiment. A case where image processing for discriminating blood vessels having an oxygen-saturation of 90% or more as arteries and blood vessels having an oxygen-saturation of less than 90% as veins is applied will be described here. In such a case, the computer 150 determines the blood vessels 31, 32, and 35 as arteries related to the region of interest 57, and the blood vessels 33 and 34 as veins related to the region of interest 57.

Next, the computer 150 calculates an average (98%) of the oxygen-saturations of the blood vessel 31, 32, and 35 corresponding to the arteries related to the region of interest 57. The computer 150 also calculates an average (67%) of the oxygen-saturations of the blood vessels 33 and 34 corresponding to the veins related to the region of interest 57. The computer 150 then calculates a difference (31%) between the average of the oxygen-saturations of the arteries related to the region of interest 57 and the average of the oxygen-saturations of the veins related to the region of interest 57. If the category criteria described in the first exemplary embodiment are applied, the tissue included in the region of interest 57 is likely to be category 4.

The computer 150 then displays an image on the display unit 160 in the display mode corresponding to the difference (31%) between the averages of the oxygen-saturations as described in the first exemplary embodiment. The computer 150 may estimate and display a final category candidate from a combination of a category candidate estimated based on the B-mode image and a category candidate estimated based on the spatial distribution of oxygen-saturation.

Here, display examples of the GUI on the display unit 160 according to the present exemplary embodiment will be described with reference to FIGS. 15A to 15D.

Figure 15A:
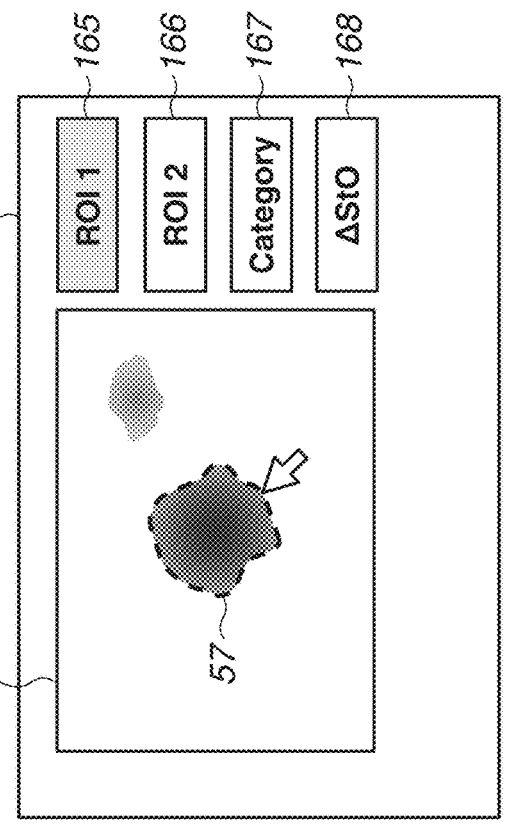
FIGS. 15A, 15B, 15C, and 15D are schematic diagrams illustrating a graphical user interface (GUI) according to the second exemplary embodiment.

FIG. 15A illustrates an example in which a B-mode image 164 is displayed. An item 165 is intended to designate a first region of interest (ROI). An item 166 is intended to designate a second region of interest. An item 167 is intended to give an instruction to display the category of the tissue included in the designated region of interest. An item 168 is intended to give an instruction to display the amount of change in the oxygen-saturation of the blood vessels related to the designated region of interest. As illustrated in FIG. 15A, if the user selects the item 165 by using the input unit 170, the computer 150 enters a mode to accept designation of the first region of interest (ROI 1). If the user designates the region of interest 57 as the first region of interest, the computer 150 obtains information indicating the region of interest 57 as information indicating the first region of interest. The computer 150 may change the display color of the item selected on the GUI so that the selected item can be identified. The item selected on the GUI may be distinguished by another display method.

Figure 15B:
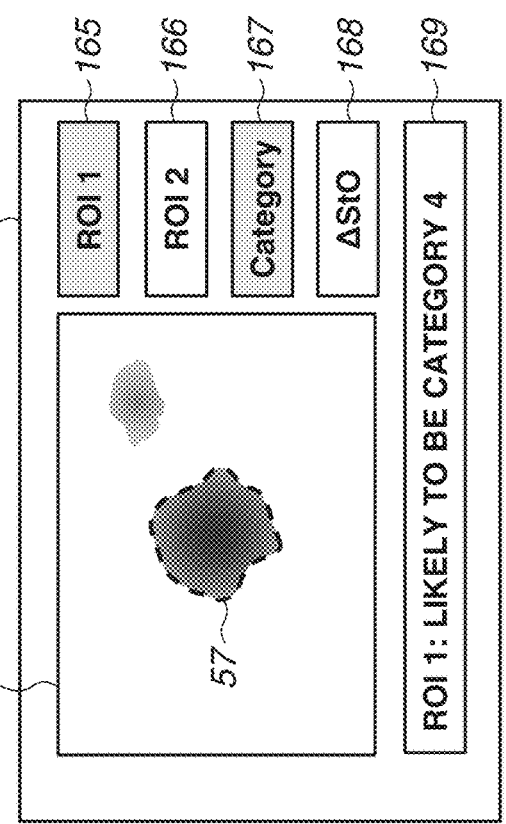

FIG. 15B illustrates a display example of the GUI when the item 167 is selected by the user after the designation of the first region of interest. If the item 167 is selected, an image 169 indicating a BI-RAD category candidate (likely category) of the tissue included in the designated region of interest 57 is displayed.

Figure 15C:
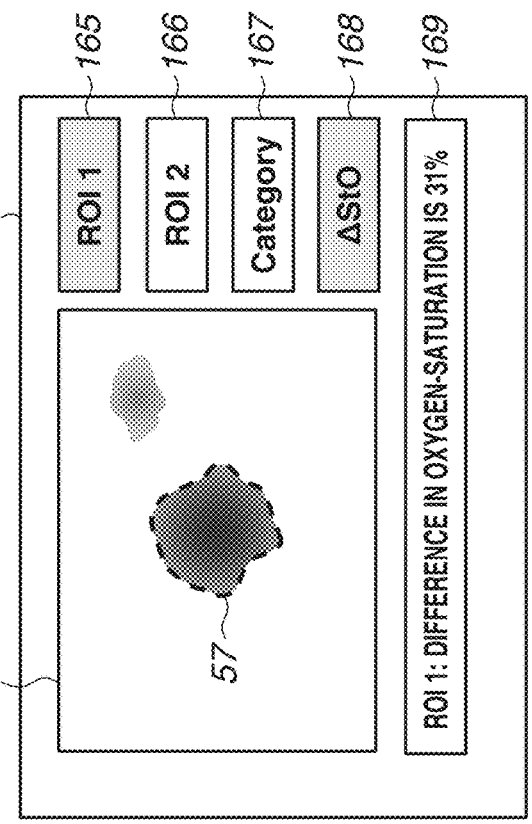

FIG. 15C illustrates a display example of the GUI when the item 168 is selected by the user after the designation of the first region of interest. If the item 168 is selected, an image 169 indicating a difference between the oxygen-saturation of the arteries and that of the veins related to the designated region of interest 57 is displayed.

Figure 15D:
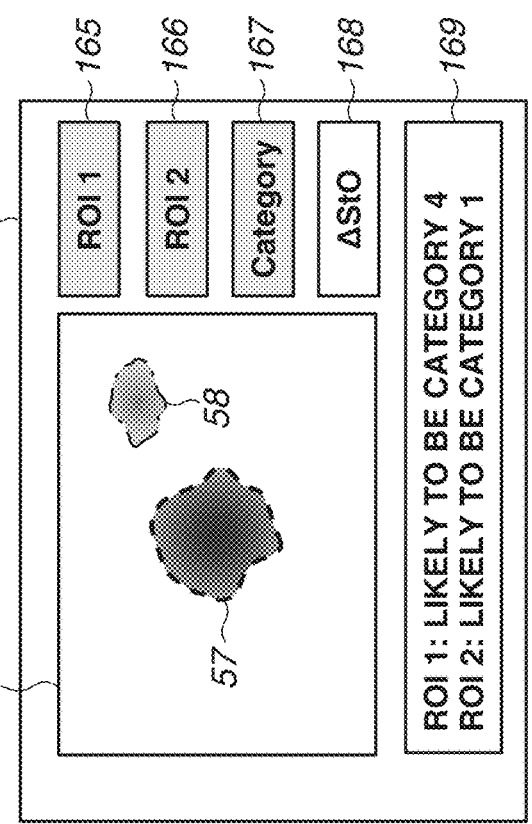

FIG. 15D illustrates a display example of the GUI when the second region of interest (ROI 2) is designated in addition to the first region of interest. If the item 166 is selected, the computer 150 enters a mode to accept designation of the second region of interest. If the user designates a region of interest 58 as the second region of interest by using the input unit 170 in such a mode, the computer 150 obtains information indicating the region of interest 58. Note that no blood vessel related to the region of interest 58 is included in the photoacoustic image data. There is therefore no change in the oxygen-saturation of the blood vessels related to the region of interest 58. If the item 167 is selected after the designation of the first and second regions of interest, an image 169 indicating that the tissue included in the region of interest 58 serving as the second region of interest (ROI 2) is likely to be BI-RAD category 1 is thus displayed. The image 169 also includes information indicating that the tissue included in the region of interest 57 serving as the first region of interest (ROI 1) is likely to be BI-RADS category 4.

As described above, FIGS. 15B, 15C, and 15D illustrate a composite image of the ultrasound image and an image indicating the condition(s) of the tissue(s) included in the region(s) of interest.

As in the present exemplary embodiment, display that can facilitate comprehension of the condition of a tissue included in a region of interest may be provided based on the spatial distribution of an oxygenation index even if no image indicating the spatial distribution of an oxygenation index is displayed. Even if it is difficult to find out the condition of the tissue from only an ultrasound image, the condition of the tissue can be easily comprehended by displaying an image indicating an estimated condition of the tissue based on the spatial distribution of oxygen-saturation.

The computer 150 may determine whether the image data stored in the storage unit 152 includes image data indicating the spatial distribution of an oxygenation index, based on information indicating an image type associated with the image data stored in the storage unit 152. If the image data stored in the storage unit 152 is determined to include the image data indicating the spatial distribution of the oxygenation index, the computer 150 may read the image data and perform the image processing according to the present exemplary embodiment. More specifically, if the computer 150 determines that the image data stored in the storage unit 152 includes the image data indicating the spatial distribution of the oxygenation index, the user can select the item 167 or 168 by using the input unit 170. On the other hand, if the image data stored in the storage unit 152 is determined to include no image data indicating the spatial distribution of the oxygenation index, the computer 150 may restrict the selection of the item 167 or 168 by the user.

In the present exemplary embodiment, the condition of the tissue is described to be estimated by using the oxygenation index. However, the condition of the tissue may be estimated in consideration of another index as well, aside from the oxygenation index. The computer 150 may estimate the condition of the tissue by using feature information obtained from image data generated by a modality other than the photoacoustic apparatus, in addition to the oxygenation index. For example, the computer 150 may obtain information indicating the hardness of at least either the blood vessels or the tissue from ultrasound image data obtained by elastography, and estimate the condition of the tissue based on the information indicating the oxygenation index and the information indicating the hardness.

In the present exemplary embodiment, an ultrasound image is described to be displayed as an image to designate a region of interest. However, an image other than an ultrasound image may be used as the image to designate a region of interest. For example, an image based on image data obtained by an imaging apparatus such as an MRI apparatus, an X-ray CT apparatus, or a PET apparatus may be used as the image to designate a region of interest.

Other Embodiments

Embodiment(s) of the present disclosure can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present disclosure has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2017-109252, filed Jun. 1, 2017, which is hereby incorporated by reference herein in its entirety.

What is claimed is:

1. An image processing apparatus comprising:
a first acquisition unit configured to obtain image data indicating a spatial distribution of an oxygenation index in a subject;
a second acquisition unit configured to obtain information indicating a region of interest including a tissue in the subject;
a third acquisition unit configured to identify a first blood vessel for supplying blood to the tissue included in the region of interest and a second blood vessel for carrying blood from the tissue included in the region of interest;
a fourth acquisition unit configured to obtain information indicating a discrepancy between the oxygenation index of the identified first blood vessel and the oxygenation index of the identified second blood vessel included in the region of interest, based on the spatial distribution of the oxygenation index and the identified first blood vessel and the identified second blood vessel, wherein the information indicates an amount of change between the oxygenation index of the identified first blood vessel and the identified second blood vessel; and
a display control unit configured to estimate a condition of the tissue included in the region of interest based on the information indicating the discrepancy in the oxygenation index,
determine a display mode of an image indicating a condition of the tissue included in the region of interest, and display the image indicating the condition of the tissue included in the region of interest on a display unit in the determined display mode.

2. The image processing apparatus according to claim 1, wherein the third acquisition unit is configured to obtain information indicating that the identified first blood vessel corresponds to an artery and the identified second blood vessel corresponds to a vein, and
wherein the display control unit is configured to:
obtain information indicating a discrepancy between a representative value of the oxygenation index of the artery and a representative value of the oxygenation index of the vein based on the image data indicating the spatial distribution of the oxygenation index and the information indicating that the identified first blood vessel corresponds to the artery and the identified second blood vessel corresponds to the vein, and
estimate the condition of the tissue included in the region of interest based on the information indicating the discrepancy.

3. The image processing apparatus according to claim 2, wherein the third acquisition unit is configured to discriminate a blood vessel of which the oxygenation index is higher than or equal to a threshold, between the identified first blood vessel and the identified second blood vessel corresponding to the artery, and discriminate a blood vessel of which the oxygenation index is lower than the threshold, as corresponding to the vein, based on the image data indicating the spatial distribution of the oxygenation index, the identified first blood vessel, and the identified second blood vessel.

4. The image processing apparatus according to claim 1, wherein the third acquisition unit is configured to determine an image overlapping with the region of interest in the image data as the identified first blood vessel and the identified second blood vessel included in the region of interest based on the image data indicating the spatial distribution of the oxygenation index and the information indicating the region of interest.

5. The image processing apparatus according to claim 1, wherein the third acquisition unit is configured to define a region having a predetermined relationship with the region of interest and determine an image overlapping with the region in the image data as the identified first blood vessel and the identified second blood vessel included in the region of interest based on the image data illustrating the spatial distribution of the oxygenation index and the information indicating the region of interest.

6. The image processing apparatus according to claim 1, wherein the first acquisition unit is configured to obtain photoacoustic image data derived from a photoacoustic wave generated by light irradiation of the subject,
wherein the display control unit is configured to display a photoacoustic image based on the photoacoustic image data on the display unit, and
wherein the second acquisition unit is configured to obtain the information indicating the region of interest based on a user's instruction on the photoacoustic image displayed on the display unit.

7. The image processing apparatus according to claim 6, wherein the display control unit is configured to display on the display unit a composite image of the photoacoustic image and the image indicating the condition of the tissue included in the region of interest.

8. The image processing apparatus according to claim 6, wherein the photoacoustic image data is the image data indicating the spatial distribution of the oxygenation index.

9. The image processing apparatus according to claim 1, wherein the first acquisition unit is configured to obtain ultrasound image data derived from transmission and reception of ultrasound to/from the subject,
wherein the display control unit is configured to display an ultrasound image based on the ultrasound image data on the display unit, and
wherein the second acquisition unit is configured to obtain the information indicating the region of interest based on a user's instruction on the ultrasound image displayed on the display unit.

10. The image processing apparatus according to claim 9, wherein the display control unit is configured to display on the display unit a composite image of the ultrasound image and the image indicating the condition of the tissue included in the region of interest.

11. The image processing apparatus according to claim 1, wherein the display control unit is configured to display an image on the display unit, the image expressing the condition of the tissue included in the region of interest by text.

12. The image processing apparatus according to claim 1, wherein the display control unit is configured to determine a candidate for a Breast Imaging Reporting and Data System (BI-RADS) category of the tissue included in the region of interest and display an image indicating the candidate for the BI-RADS category on the display unit based on the oxygenation index of the identified first blood vessel and the identified second blood vessel included in the region of interest.

13. The image processing apparatus according to claim 1, wherein the first acquisition unit is configured to obtain image data different from the image data indicating the spatial distribution of the oxygenation index, and
wherein the display control unit is configured to display an image on the display unit, the image including the image indicating the condition of the tissue included in the region of interest and an image based on the image data different from the image data indicating the spatial distribution of the oxygenation index but not including an image based on the image data indicating the spatial distribution of the oxygenation index.

14. The image processing apparatus according to claim 1, wherein the oxygenation index is oxygen-saturation.

15. The image processing apparatus according to claim 1, wherein the fourth acquisition unit is configured to obtain information indicating at least one of a difference, a ratio, and variations in the oxygenation index of the identified first blood vessel and the identified second blood vessel included in the region of interest as the information indicating the discrepancy in the oxygenation index of the blood vessel related to the region of interest.

16. An image processing method comprising:
   obtaining image data indicating a spatial distribution of an oxygenation index in a subject;
   obtaining information indicating a region of interest including a tissue in the subject;
   identifying a first blood vessel for supplying blood to the tissue included in the region of interest and a second blood vessel for carrying blood from the tissue included in the region of interest;
   obtaining information indicating a discrepancy between the oxygenation index of the identified first blood vessel and the oxygenation index of the identified second blood vessel included in the region of interest, based on the image data indicating the spatial distribution of the oxygenation index and the identified first blood vessel and the identified second blood vessel, wherein the information indicates an amount of change between the oxygen index of the identified first blood vessel and the identified second blood vessel;
   estimating a condition of the tissue included in the region of interest based on the information indicating the discrepancy in the oxygenation index;
   determining a display mode of an image indicating a condition of the tissue included in the region of interest; and
   displaying the image indicating the condition of the tissue included in the region of interest in the determined display mode.

17. A non-transitory storage medium storing a program for causing a computer to perform:
   obtaining image data indicating a spatial distribution of an oxygenation index in a subject;
   obtaining information indicating a region of interest including a tissue in the subject;
   identifying a first blood vessel for supplying blood to the tissue included in the region of interest and a second blood vessel for carrying blood from the tissue included in the region of interest;
   obtaining information indicating a discrepancy between the oxygenation index of the identified first blood vessel and the oxygenation index of the identified second blood vessel included in the region of interest, based on the spatial distribution of the oxygenation index and the identified first blood vessel and the identified second blood vessel, wherein the information indicates an amount of change between the oxygen index of the identified first blood vessel and the identified second blood vessel;
   estimating a condition of the tissue included in the region of interest based on the information indicating the discrepancy in the oxygenation index;
   determining a display mode of an image indicating a condition of the tissue included in the region of interest; and
   displaying the image indicating the condition of the tissue included in the region of interest in the determined display mode.

* * * * *